(12) United States Patent
Burrows et al.

(10) Patent No.: US 9,926,360 B2
(45) Date of Patent: Mar. 27, 2018

(54) MONOMERIC RECOMBINANT MHC MOLECULES USEFUL FOR MANIPULATION OF ANTIGEN-SPECIFIC T-CELLS

(71) Applicants: Oregon Health & Science University, Portland, OR (US); The United States Government as Represented by the Department of Veterans Affairs, Washington, DC (US)

(72) Inventors: Gregory G. Burrows, Portland, OR (US); Arthur A. Vandenbark, Portland, OR (US)

(73) Assignees: Oregon Health & Science University, Portland, OR (US); The United States of America as represented by the Deparment of Veterans Affairs, Washington, DC (US)

( * ) Notice: Subject to any disclaimer, the term of this patent is extended or adjusted under 35 U.S.C. 154(b) by 0 days.

(21) Appl. No.: 14/973,033

(22) Filed: Dec. 17, 2015

(65) Prior Publication Data
US 2016/0102132 A1    Apr. 14, 2016

Related U.S. Application Data

(63) Continuation of application No. 13/731,711, filed on Dec. 31, 2012, now Pat. No. 9,243,051, which is a continuation of application No. 10/936,467, filed on Sep. 7, 2004, now Pat. No. 8,377,447.

(60) Provisional application No. 60/500,660, filed on Sep. 5, 2003.

(51) Int. Cl.
*A61K 39/00* (2006.01)
*C07K 14/705* (2006.01)
*C07K 14/74* (2006.01)
*C12N 15/62* (2006.01)
*C12N 15/86* (2006.01)

(52) U.S. Cl.
CPC ........ *C07K 14/705* (2013.01); *A61K 39/0008* (2013.01); *C12N 15/62* (2013.01); *C12N 15/86* (2013.01)

(58) Field of Classification Search
None
See application file for complete search history.

(56) References Cited

U.S. PATENT DOCUMENTS

| | | | |
|---|---|---|---|
| 5,130,297 A | 7/1992 | Sharma et al. | |
| 5,194,425 A | 3/1993 | Sharma et al. | |
| 5,260,422 A | 11/1993 | Clark et al. | |
| 5,284,935 A | 2/1994 | Clark et al. | |
| 5,468,481 A | 11/1995 | Sharma et al. | |
| 5,569,585 A | 10/1996 | Goodwin et al. | |
| 5,583,031 A | 12/1996 | Stern | |
| 5,595,881 A | 1/1997 | Kendrick et al. | |
| 5,635,363 A | 6/1997 | Altman et al. | |
| 5,734,023 A | 3/1998 | Nag et al. | |
| 5,869,270 A | 2/1999 | Rhode et al. | |
| 5,976,551 A | 11/1999 | Mottez et al. | |
| 6,106,840 A | 8/2000 | Clark et al. | |
| 6,232,445 B1 | 5/2001 | Rhode et al. | |
| 6,270,772 B1 | 8/2001 | Burrows et al. | |
| 6,815,171 B2 | 11/2004 | Burrows et al. | |
| 7,265,218 B2 | 9/2007 | Burrows et al. | |
| 2002/0091079 A1 | 7/2002 | Rhode et al. | |
| 2002/0187148 A1 | 12/2002 | Germain et al. | |
| 2002/0198144 A1 | 12/2002 | Wong et al. | |
| 2003/0007978 A1 | 1/2003 | Burrows et al. | |
| 2005/0142142 A1 | 6/2005 | Burrows et al. | |
| 2008/0064859 A1 | 3/2008 | Vandenbark et al. | |

FOREIGN PATENT DOCUMENTS

| | | |
|---|---|---|
| WO | WO 95/23814 | 9/1995 |
| WO | WO 96/04314 | 2/1996 |
| WO | WO 96/26962 | 9/1996 |
| WO | WO 96/40944 | 12/1996 |
| WO | WO 97/28191 | 8/1997 |
| WO | WO 99/09064 | 2/1999 |
| WO | WO 99/14236 | 3/1999 |

OTHER PUBLICATIONS

Sinha et al (J. Neuroimmune Pharmacol., Springer Science and Business Media, DOI 10.1007/s11481-009-9175-1, published online Sep. 30, 2009, 9 pages).*
Titelbaum et al (Am. J. Neuroradiol., 2005, 26: 1548-1550).*
Zanelli et al (Rheum. 2000 39: 1060-1066).*
Altman et al., "Phenotypic Analysis of Antigen-Specific T Lymphocytes," *Science*, vol. 274, pp. 94-96, 1996.
Besong et al., "Activation of group III metabotropic glutamate receptors inhibits the production of RANTES in glial cell cultures," *Journal of Neuroscience*, vol. 22, No. 13, pp. 5403-5411, 2002.
Burrows et al., "Design, engineering and production of functional single-chain T cell receptor ligands," *Protein Engineering*, vol. 12, No. 9, pp. 771-778, 1999.
Burrows et al., "Regulation of Encephalitogenic T Cells With Recombinant TCR Ligands," *Journal of Immunology*, vol. 164, No. 12, pp. 6366-6371, 2000.
Burrows et al., "Two-Domain MHC Class II Molecules Form Stable Complexes With Myelin Basic Protein 69-89 Peptide That Detect and Inhibit Rat Encephalitogenic T-Cells and Treat Experimental Autoimmune Encephalomyelitis," *Journal of Immunology*, vol. 161, pp. 5987-5996, 1998.

(Continued)

*Primary Examiner* — Gerald R Ewoldt
*Assistant Examiner* — Marianne Dibrino
(74) *Attorney, Agent, or Firm* — Klarquist Sparkman, LLP

(57) ABSTRACT

The present invention provides, in particular embodiments, for modified recombinant T cell receptor (TCR) ligands (RTLs) comprising a MHC class I or MHC class II component. The modified RTLs have redesigned surface features that preclude or reduce aggregation, wherein the modified molecules retain the ability to bind Ag-peptides, target antigen-specific T cells, inhibit T cell proliferation in an Ag-specific manner and have utility to treat, inter alia, autoimmune disease and other conditions mediated by antigen-specific T cells in vivo.

12 Claims, 5 Drawing Sheets

(56) References Cited

OTHER PUBLICATIONS

Chang et al., "Design, engineering, and production of human recombinant T cell receptor ligands derived from human leukocyte antigen DR2," *J. Biol. Chem.*, vol. 276, pp. 24170-24176, 2001.

Chou et al., "MHC-restriction, cytokine profile, and immunoregulatory effects of human T cells specific for TCR Vβ CDR2 peptides: Comparison with myelin basic protein-specific T cells," *Journal of Neuroscience Research*, vol. 45, pp. 838-851, 1996.

Fremont et al., "Structures of an MHC Class II Molecule with Covalently Bound Single Peptides," *Science*, vol. 272, No. 5264, pp. 1001-1004, 1996.

Hass et al., "Preparation of Synthetic Polypeptide Domains of Carcinoembryonic Antigen and Their Use in Epitope Mapping," *Cancer Research*, vol. 51, No. 7, pp. 1876-1882, 1991.

Huan et al., "Rationally designed mutations convert complexes of human recombinant T cell receptor ligands into monomers that retain biological activity," *J. Chem. Technol. Biotechnol.*, vol. 80, pp. 2-12, 2005.

Kozono et al., "Production of Soluble MHC Class II Proteins with Covalently Bound Single Peptides," *Nature*, vol. 369, pp. 151-154, 1994.

Krogsgaard et al., "Visualization of myelin basic protein (MBP) T cell epitopes in multiple sclerosis lesions using a monoclonal antibody specific for the human histocompatibility leukocyte antigen (HLA)-DR2-MBP 85-99 complex," *J. Exp. Med.*, vol. 191, pp. 1395-1412, 2000.

Kuerten et al., ("MP4- and MOG:35-55-induced EAE in C57BL/6 mice differentially targets brain, spinal cord and cerebellum," *J. Neuroimmunol.* 189:31-40, 2007.

Li et al., "Structural Basis for the Binding of an Immunodominant Peptide From Myelin Basic Protein in Different Registers by Two HLA-DR2 Proteins," *Journal of Molecular Biology*, vol. 304, No. 2, pp. 177-188, 2000.

McFarland et al., "Determinant Spreading Associated with Demyelination in a Nonhuman Primate Model of Multiple Sclerosis," *J. Immunol.* 162:2384-2390, 1999.

McMahan et al., "Production, Characterization, and Immunogenicity of a Soluble Rat Single Chain T Cell Receptor Specific for an Encephalitogenic Peptide," *J. Biol. Chem.* vol. 278, No. 33, pp. 30961-30790, 2003.

Ngo et al, "The Protein Folding Problem and Tertiary Structure Prediction," Merz and Legrand, Editors, pp. 492-495, 1994.

Ngo et al., "Computational Complexity, Protein Structure Prediction, and the Levinthal Paradox," *The Protein Folding Problem and Tertiary Structure Prediction*, Merz and LeGrand (eds.), pp. 491-495, 1994.

Nieba et al., "Disrupting the hydrophobic patches at the antibody variable/constant domain interface: improved in vivo folding and physical characterization of an engineered scFv fragment," *Protein Engineering*, vol. 10, No. 4, pp. 435-444, 1997.

Quill and Schwartz, "Stimulation of Normal Inducer T Cell Clones with Antigen Presented by Purified Ia Molecules in Planar Lipid Membranes: Specific Induction of a Long-Lived State of Proliferative Nonresponsiveness," *Journal of Immunology*, vol. 138, No. 11, pp. 3704-3712, 1987.

Rammensee et al, MHC Ligands and Peptide Motifs, Landes Bioscience. Springer, Austin, TX, USA, pp. 55-60, 1997.

Rhode et al., "Single-Chain MHC Class II Molecules Induce T Cell Activation and Apoptosis," *Journal of Immunology*, vol. 157, No. 11, pp. 4885-4891, 1996.

Smith et al., "Crystal Structure of HLA-DR2 (DRA*0101, DRB1*1501) Complexed With a Peptide From Human Myelin Basic Protein," *J. Exp. Med.*, vol. 188, No. 8, pp. 1511-1520, 1998.

Spack et al., "Induction of Tolerance in Experimental Autoimmune Myasthenia Gravis with Solubilized MHC Class II:Acetylcholine Receptor Peptide Complexes," *Journal of Autoimmunity*, vol. 8, No. 6, pp. 787-807, 1995.

Syha et al., "Complete cDNA sequence coding for the MHC class II RT1.B chain of the Lewis rat," *Nucleic Acids Research*, vol. 17, p. 3985, 1989.

Syha-Jedelhauser et al., "Complete coding nucleotide sequence of cDNA for the class II RT1.B chain of the Lewis rat," *Biochimica et Biophysica Acta*, vol. 1089, pp. 414-416, 1991.

Tisch and McDevitt, "Antigen-specific immunotherapy: is it a real possibility to combat T-cell-mediated autoimmunity?," *Proc. Natl. Acad. Sci. USA.*, vol. 91, pp. 437-438, 1994.

Tzartos et al., "Role of the main immunogenic region of acetylcholine receptor in myasthenia gravis. An Fab monoclonal antibody protects against antigenic modulation by human sera," *J. Immunol.*, vol. 134, No. 4, pp. 2343-2349, 1985.

Vandenbark et al., "Recombinant TCR Ligand Induces Tolerance to Myelin Oligodendrocyte Glycoprotein 35-55 Peptide and Reverses Clinical and Histological Signs of Chronic Experimental Autoimmune Encephalomyelitis in HLA-DR2 Transgenic Mice," *J. Immunol.* vol. 171, pp. 127-133, 2003.

Wekerle et al., "Autoimmunity's Next Top Models," *Nature Med.*, vol. 18, No. 1, pp. 66-70, 2012.

Yadav et al, "Recombinant T-Cell Receptor Ligand (RTL) for Treatment of Multiple Sclerosis: A Double-Blind, Placebo-Controlled, Phase 1, Dose-Escalation Study," *Autoimmune Diseases*, vol. 77, No. 6, pp. 1-11, 2012.

Zeng et al., "Crystal Structure of Mouse CD1: An MHC-Like Fold with a Large Hydrophobic Binding Groove," *Science*, vol. 277, pp. 339-345, 1997.

EverythingBio, available on the World Wide Web at everythingbio.com/glos/definition/php?ID=318, Sep. 2011.

International Search Report for Application No. PCT/US04/29096, dated Jul. 27, 2005.

* cited by examiner

MONOMERIC RECOMBINANT MHC MOLECULES USEFUL FOR MANIPULATION OF ANTIGEN-SPECIFIC T-CELLS

CROSS REFERENCES TO RELATED APPLICATIONS

This is a continuation of U.S. patent application Ser. No. 13/731,711, filed Dec. 31, 2012, which is a continuation of U.S. patent application Ser. No. 10/936,467, filed Sep. 7, 2004, now U.S. Pat. No. 8,377,447, issued Feb. 19, 2013, which claims the benefit of U.S. Provisional Patent Application No. 60/500,660, filed Sep. 5, 2003, each of which are incorporated herein by reference.

STATEMENT REGARDING FEDERALLY-SPONSORED RESEARCH

Aspects of this work were supported by grants from the National Institutes of Health (A143960, ESI0554 and NS41965), the National Multiple Sclerosis Society (RG3012A), and the Department of Veterans Affairs. The United States government has certain rights in the subject matter.

FIELD OF THE INVENTION

The present invention relates to recombinant polypeptides comprising major histocompatibility complex (MHC) molecular domains that mediate antigen binding and T cell receptor (TCR) recognition, and to related compositions and methods incorporating these recombinant polypeptides. The compositions and methods of the invention are useful for detection, quantification, and purification of antigen-specific T cells, for modulating T cell activity, and for treating T cell mediated diseases such as autoimmune disorders.

BACKGROUND OF THE INVENTION

The immune system ordinarily functions to direct protective immune responses against microorganisms and other harmful foreign materials. In the context of autoimmune diseases and transplant rejection, however, these normally beneficial immune responses can mediate deleterious and often fatal effects. In the case of autoimmunity, antigens present in the body's own tissues become targets for auto-reactive immune responses that cause tissue destruction and other disease symptoms.

Immune responses in mammals are mediated by a diverse array of peripheral blood cells called leukocytes. Leukocytes arise from hematopoietic stem cells which undergo self-renewal and differentiation into two precursor lineages—the myeloid and lymphoid lines. Further differentiation occurs among these lineages to produce monocyte, eosinophil, neutrophil, basophil, megakaryocyte, and erythroid cells from the myeloid line, and T lymphocytes, B lymphocytes, and NK cells from the lymphoid line.

T lymphocytes include CD8+ T cells (cytotoxic/suppressor T cells), and CD4+ T cells distinguished in part by their expression of cell surface molecules, CD8, and CD4, respectively, which function to enhance the avidity with which T cells bind antigen-bearing or target cells, and may also promote the interaction of the TCR with cognate antigen. Bierer et al., *Ann. Rev. Immunol.* 7:579-99, 1989.

CD4+ T cells play a key regulatory role with respect to other immune system cell types, acting as "T helper" or "T inducer" cells when activated. By virtue of this central regulatory role, CD4+ T cells are key players in the pathogenesis of various autoimmune diseases, including multiple sclerosis (MS), rheumatoid arthritis (RA), diabetes, sarcoidosis, autoimmune uveitis, chronic beryllium disease, and are also considered to play a causal role in transplant rejection and graft-versus-host disease (GVHD) (Swanborg, *J. Immunol* 130:1503-05, 1983; Cush. *Arthritis Rheum.* 31: 1230-38, 1988; Caspi, *J. Immunol* 140:1490-95, 1988; Cobbold et al., *Nature* 312:54851, 1988; Steinman, *Sci. Am.* 269:106-14, 1993).

CD4+ T cells mediate their role in autoimmune disease by responding in an antigen-specific manner to "autoantigens" associated with target cells or tissues. Pathogenic CD4+ T cells migrate or "home" to target tissues bearing autoantigen and selectively produce T-helper type 1 (Th1) cytokines, which trigger recruitment and activation of other lymphocytes and monocytes that may destroy target tissues and cause other adverse disease sequelae (Weinberg, et al., *J. Immunol* 148:2109-17, 1992; Weinberg et al., *J. Immunol* 152:4712-5721, 1994).

Normal activation of T lymphocytes occurs when the T cells interact with antigen-presenting cells (APCs) bearing cognate antigen (Ag) in the context of a major histocompatibility complex (MHC) protein. The specificity of T cell responses is conferred by a polymorphic, antigen-specific T cell receptor (TCR). T cell activation is mediated by TCR recognition of the Ag presented on the surface of the APC as a processed peptide bound to the MHC molecule.

Two distinct classes of MHC molecules occur in humans and other mammals, termed MHC class I and MHC class II. Both classes of MHC molecules comprise complexes formed by association of multiple polypeptide chains, and each includes a trans-membrane portion that anchor the complex into the APC membrane. MHC class I molecules are comprised of an α-polypeptide chain non-covalently associated with a β2-microglobulin chain. The α-chain of MHC class I includes three distinct domains, termed the α1, α2 and α3 domains. The three-dimensional structure of the α1 and α2 domains of MHC I molecules forms a peptide binding groove (alternatively referred to herein as the peptide binding cleft or pocket) which binds cognate Ag for presentation to T-cells. The αβ domain is an Ig-fold like domain that includes a trans-membrane sequence to anchor the α-chain into the cell membrane of the APC. MHC class I complexes, when associated with antigen in the presence of appropriate co-stimulatory signals, stimulate CD8+ cytotoxic T-cells to kill target cells in an Ag-specific manner.

The genes that encode the various polypeptide chains that associate to form MHC complexes in mammals have been studied and described in extensive detail. In humans, MHC molecules (with the exception of class I β2-microglobulin) are encoded in the HLA region of the genome, located on chromosome 6. There are three class I MHC α-chain-encoding loci, termed HLA-A, HLA-B and HLA-C. In the case of MHC class II proteins, there are three pairs of α and β chain loci, termed HLA-DR(A and B), HLA-DP(A and B), and HLA-DQ(A and B). In rats, the class I α gene is designated RT1.A, while the class II genes are termed RT1.B α and RT1.B β. More detailed description regarding the structure, function and genetics of MHC complexes can be found, for example, in Immunobiology: The Immune System in Health and Disease by Janeway and Travers, Current Biology Ltd./Garland Publishing, Inc. (1997), and in Bodmer et al. (1994) "Nomenclature for factors of the HLA system" Tissue Antigens vol. 44, pages 1-18.

The specificity of T cell responses is conferred by a polymorphic, antigen-specific T cell receptor (TCR). TCRs comprise multi-chain, α/β heterodimeric receptors, which are activated in an Ag-specific manner by Ag processed and presented on the surface of APCs as a peptide bound to the MHC complex. X-ray crystallographic data demonstrate that peptides from processed antigen bind to MHC II proteins in a membrane distal pocket formed by the β1 and α1 domains (Matsui et al., *Science* 254:1788-91, 1991; Nag et al., *J. Biol. Chem.* 267:22624-29, 1992).

CD4[+] T cell activation generally follows a multi-step course that includes co-ligation of the TCR and CD4 by the MHC class II/peptide complex presented by APCs. A separate activation event referred to as "co-stimulation" is mediated by other T cell surface molecules, such as CD28. In the absence of the second, co-stimulatory signal, stimulation of T cells through the TCR by MHC class II/peptide complex reportedly induces a state of unresponsiveness to subsequent optimal antigen presentation, commonly referred to as "anergy". (Quill, *J. Immunol* 138:3704-12, 1987; Schwartz, *J. Exp. Med.* 184:1-8, 1996). In other studies, ligation of the TCR in the absence of a costimulatory signal has been reported to disrupt normal T cell activation, inducing a range of responses from anergy to apoptosis (Schwartz, *J. Exp. Med.* 184:1-8, 1996; Janeway, *Cell* 76:275-85, 1994; Burrows et al., *J. Immunol* 167:4386-95, 2001; Wang et al., *The Journal of Immunology*, 2003).

MHC-restricted T lymphocyte interactions have been widely and extensively investigated. Cells of the T helper/inducer subset generally recognize antigen on the surface of APCs only in association with class II MHC gene products, which results in genetic restriction of antigen recognition. While the rules governing the activation of MHC-restricted T cells, and particularly of class II MHC-restricted T cells, have been well described, the underlying mechanisms are still being defined.

Despite the very large number of possible TCR specificities of T cells, a number of studies have shown that the major portion of the T cell response to protein antigens may be directed to a few "immunodominant" epitopes within the antigenic protein. In the context of autoimmune diseases, class II MHC-restricted T cell responses, and in some cases clinical signs of autoimmune disease, have been demonstrated to be associated with specific proteins and/or immunodominant epitopes from these proteins, including, e.g., type II collagen (Rosloneic et al., *J. Immunol.* 160:2573-78, 1998; Andersson et al., *Proc. Natl. Acad. Sci. USA* 95:7574-79, 1998; and Fugger et al., *Eur. J. Immunol*, 26:928-33, 1996), and human cartilage Ag gp39 (Cope et al., *Arthritis Rheum.* 42:1497, 1999) associated with rheumatoid arthritis (RA), glutamic acid decarboxylase 65 (Patel et al., *Proc. Natl. Acad. Sci. USA* 94:8082-87, 1997; Wicker et al., *J. Clin. Invest.* 98:2597, 1996) and insulin (Congia et al., *Proc. Natl. Acad. Sci. USA* 95:3833-38, 1998) associated with Type 1 diabetes (insulin dependent diabetes mellitus or IDDM), and myelin oligodendrocyte glycoprotein (MOG) (Forsthuber et al., *J. Immunol.* 167:7119, 2001) associated with MS and an animal disease model for MS, experimental autoimmune encephalomyelitis (EAE). Similar findings have been reported for class II MHC-restricted T cell responses associated with myelin basic protein (MBP) (Madsen et al., *Nat. Genet*, 23:343, 1999), proteolipid protein (PLP) (Kawamura et al., *J. Clin. Invest*, 105:977, 2000), and MOG (Vandenbark et al., *J. Immunol.* 171:127-33, 2003).

One approach for managing and treating autoimmune diseases and other T cell-mediated immune disorders is to regulate T cell activity using natural or synthetic TCR ligands, or T cell modulatory drugs or other compounds, that are TCR agonists or antagonists. Various analogs of natural TCR ligands have been produced which comprise extracellular domains of class II MHC molecules bound to a specific peptide Ag. Several such constructs have been purified as detergent extracts of lymphocyte membranes or produced as recombinant proteins (Sharma et al., *PNAS*. 88:11465-69, 1991), Kozono et al., *Nature* 369:151-54, 1994; Arimilli et al., *J. Biol. Chem.* 270:971-77, 1995; Nag, *PNAS* 90:1604.08, 1993; Nag et al., *J. Biol. Chem.* 271:10413-18, 1996; Rhode et al., *J. Immunol.* 157:4885-91, 1996; Fremont et al., *Science* 272:1001, 1996; Sharma et al., *Proc. Natl. Acad. Sci. USA* 88:11405, 1991; Nicolle et al., *J. Clin. Invest.* 93:1361, 1994; Spack et al., *CNS Drug Rev.* 4: 225, 1998).

These two-chain, four-domain molecular complexes loaded with, or covalently bound to, peptide Ag have been reported to interact with T cells and modulate T cell activity in an Ag-specific manner (Matsui et al., *Science* 254:1788-91, 1991; Nag et al., *J. Biol. Chem,* 267:22624-29, 1992; Nag, *J. Biol. Chem.* 268:14360-14366, 1993; Nag, *PNAS* 90:1604-08, 1993; Nicolle et al., *J. Clin. Invest.* 93:1361-1369, 1994; Spack et al., *J. Autoimmun.* 8:787-807, 1995). Various models have been presented for how these complexes may be useful to modulate immune responses in the context of autoimmune disease. For example, U.S. Pat. No. 5,194,425 (Sharma et al.) and U.S. Pat. No. 5,284,935 (Clark et al.) report the use of isolated MHC class II/peptide complexes conjugated to a toxin to eliminate autoreactive T-cells. Others have reported the use of MHC II/antigen complexes, in the absence of co-stimulatory factors, to induce a state of non-responsiveness in Ag-specific T cells known as "anergy" (Quill et al., J. Immunol., 138:3704-3712 (1987). Following this observation, Sharma et al. (U.S. Pat. Nos. 5,468,481 and 5,130,297) and Clarke et al. (U.S. Pat. No. 5,260,422) suggested that soluble MHC II/antigen complexes can be administered therapeutically to anergize T-cell lines that specifically respond to autoantigenic peptides. Additional studies report that soluble MHC II/antigen complexes can inhibit 1' cell activation, induce T cell anergy, and/or alleviate T cell-mediated symptoms of autoimmune disease (Sharma et al., *Proc. Natl. Acad. Sci. USA* 88:11405, 1991; Spack et al., *CNS Drub Rev.* 4: 225, 1998; Steward et al., *J. Allerg. Clin. Immun.* 2:S117, 1997). In some cases, in the absence of co-stimulation, intact MHC class II/peptide complexes have been reported to modulate T cell activity by inducing antigen-specific apoptosis rather than anergy (Nag et al., *J. Biol. Chem.* 271:10413-18, 1996). Although the concept of using isolated MHC/antigen complexes in therapeutic and diagnostic applications holds great promise, a major drawback to the various methods reported to date is that the complexes are large and consequently difficult to produce and work with. While these four domain complexes can be isolated from lymphocytes by detergent extraction, such procedures are inefficient and yield only small amounts of protein. Although cloning of genes encoding MHC complex subunits has facilitated production of large quantities of individual subunits through expression in prokaryotic cells, the assembly of individual subunits into MHC complexes having appropriate conformational structure has proven difficult. Another important feature of these previously described, MHC II/antigen complexes is that they bind not only to the TCR, but also to the CD4 molecule on the T cell surface through the β2 MHC domain (Brogdon et al., *J. Immunol.* 161:5472, 1998). This additional interaction during peptide presentation and TCR engagement complicates the usefulness of prior MHC II/antigen complexes for certain diagnostic and therapeutic applications. In addition, because of their size and complex structure, prior class II MHC complexes present an inherently difficult in vitro folding challenge.

To overcome these obstacles and provide additional advantages, inventors in the current application previously developed novel, recombinant TCR ligands or "RTLs" for use in modulating T cell activity. These RTLs incorporate selected structural components of a native MHC class II protein, typically comprising MHC class II α1 and β1 domains (or portions of the α1 and β1 domains necessary to form a minimal, Ag-binding pocket/TCR interface). These RTLs may exclude all or part of the β2 domain of the MHC class II protein, typically at least the CD4-binding portion of the β2 domain. Likewise, RTLs for use within the invention may exclude the α2 domain of the MHC class II protein (see, e.g., Burrows et al., *Prot. Eng.* 12:771, 1999). Various RTLs having these general structural characteristics been produced in *E. coli*, with and without amino-terminal extensions comprising covalently bound, peptide Ag.

These kinds of RTL constructs have been demonstrated to be effective agents for alleviating symptoms of CD4+ T cell-mediated autoimmune disease in an MHC-specific, Ag-specific manner (Burrows et al., *J. Immunol* 167:4386-95, 2001; Vandenbark et al., *Journal of immunology*, 2003). For example, RTL constructs have been tested and shown to prevent and/or treat MBP-induced EAE in Lewis rats (Burrows et al., *J. Immunol.* 161:5987, 1998; Burrows et al., *J. Immunol.* 164:6366, 2000) and to inhibit activation and induce IL-10 secretion in human DR2-restricted T cell clones specific for MBP-85-95 or BCR-ABL b3a2 peptide (CABL) (Burrows et al., *J. Immunol.* 167:4386, 2001; Chang et al., *J. Biol. Chem.* 276:24170, 2001). Another RTL construct designed by inventors in the current application is a MOG-35-55/DR2 construct (VG312) that potently inhibits autoimmune responses and elicits immunological tolerance to encephalitogenic MOG-35-55 peptide, and alleviates or reverses clinical and histological signs of EAE (Vandenbark et al., *J. Immunol.* 171:127-33, 2003). Numerous additional RTL constructs useful for modulating T cell immune responses have been developed by the current inventors, which can be effectively employed within the compositions and methods of the instant invention (see, e.g., Huan et al., *J. Immunol.* 172:4556-4566, 2004).

In recently described protein engineering studies of RTLs, applicants discovered that MHC class II-derived RTL molecules can form undesirable aggregates in solution. In the case of one RTL construct derived from HLA-DR2 (DRB1*1501/DRA*0101)), the purified RTL yielded approximately 10% of the molecules in the form of stable dimers, with a remaining percentage of the molecules found in the form of higher-order structures above 300,000 Daltons (Chang et al., *J. Biol. Chem.* 276:24170-76, 2001).

Although RTL aggregates retain biological activity (Burrows et al., *J. Immunol* 167:4386-95, 2001; Vandenbark et al., *Journal of Immunology* 171:127-133, 2003), conversion of multimeric RTLs into a monodisperse reagents in solution remains an important, unfulfilled objective to facilitate use of RTLs as human therapeutics, for example to treat multiple sclerosis and other autoimmune conditions.

Accordingly, there remains an unmet need in the art to provide recombinant TCR ligands (RTLs) that retain the ability to bind Ag peptides and interface functionally with a TCR to modulate T cell activity in an Ag-specific manner, which have diagnostic and/or therapeutic utility, and which exhibit a reduced potential for aggregation in solution or following administration to a mammalian subject.

SUMMARY OF THE INVENTION

The present invention satisfies this need and fulfills additional objects and advantages by providing modified, recombinant T cell receptor ligands (RTLs) that have been structurally modified to exhibit a diminished propensity for self-aggregation. Modified RTLs of the invention typically have one or more redesigned surface structural features introduced into an otherwise native MHC polypeptide sequence. For example, modified RTLs can be rationally designed and engineered to introduce one or more amino acid changes at a solvent-exposed target site for modification located within, or defining, a self-binding (or self-associating) interface found in the native MHC polypeptide.

Within exemplary embodiments of the invention, the modified RTL includes a multi-domain structure comprising multiple MHC class I or MHC class II domains, or portions thereof necessary to form a minimal TCR interface necessary to mediate Ag binding and TCR recognition.

In the case of modified RTLs derived from human class II MHC molecules, the RTLs typically comprise α1 and β1 MHC polypeptide domains (or portions thereof sufficient to provide a minimal TCR interface) of an MHC class II protein. These domains or subportions thereof may be covalently linked to form a single chain (sc) MHC class II polypeptide. The resulting MHC component may be useful as an "empty" RTL, or may be associated with a peptide Ag.

Modified RTL molecules of the invention show improved characteristics of monodispersal in aqueous solutions, while retaining their ability to bind peptide Ags, to target and modulate activity of antigen-specific T cells, and to treat, inter cilia, autoimmune diseases and other conditions mediated by antigen-specific T cells in vivo.

The modified RTLs of the invention lack certain structural features found in intact, native MHC molecules (e.g., transmembrane Ig fold domains), but nonetheless are capable of refolding in a manner that is structurally analogous to native whole MHC molecules. The modified RTLs are likewise capable of binding peptide Ags to form stable MHC:antigen complexes. Moreover, these modified RTLs, when associated with a cognate peptide Ag, bind T-cells in an epitope-specific manner, and regulate T cell activity (e.g., proliferation) in an Ag-specific manner, both in vitro and in vivo. As a result, the disclosed MHC molecules are useful in a wide range of both in vivo and in vitro applications.

Various formulations of modified, monodisperse RTLs are provided by the invention. In exemplary embodiments, a modified RTL comprises a two domain MHC class II component comprising α1 and β1 domains of a mammalian MHC class II molecule. In more detailed embodiments, these modified RTLs are further characterized by having the amino terminus of the α1 domain covalently linked to the carboxy terminus of the β1 domain. In other detailed embodiments, the MHC component of the RTL does not include α2 or β2 domains found in an intact MHC class II molecule. Typically, the MHC component of the RTL is associated, by covalent or non-covalent interaction, with an antigenic determinant, such as a T cell epitope of an autoantigenic protein. For example, a peptide antigen may be covalently linked to the amino terminus of the β1 domain of a class II MHC component. The two domain molecules may also comprise a detectable marker, such as a fluorescent label, or a toxic moiety (e.g., ricin A).

The invention also provides nucleic acid molecules that encode the inventive, non-aggregating RTLs, as well as expression vectors that may be used to express these molecules in mammalian cells. In particular embodiments, the nucleic acid molecules include sequences that encode the MHC component as well as an antigenic peptide. For example, one such nucleic acid molecule may be represented by the formula Pr—P—B-A, wherein Pr is a promoter sequence operably linked to P (a sequence encoding the peptide antigen). B is the class II β1 domain, and A is the class II α1 domain. In these nucleic acid molecules, P, B and A comprise a single open reading frame, such that the peptide and the two MHC domains are expressed as a single polypeptide chain.

The modified RTLs of the invention may be used in vivo to detect and quantify T-cells, and/or to regulate T cell function. Specifically, such molecules loaded with a selected antigen may be used to detect, monitor and quantify the population of antigen-specific T cells, providing utility, inter alia, in a number of clinical settings, such as monitoring the number of tumor antigen-specific T cells in blood removed from a cancer patient, or the number of self-antigen specific T cells in blood removed from a patient suffering from an autoimmune disease. In these contexts, the disclosed molecules are powerful tools for monitoring the progress of a particular therapy.

In addition to monitoring and quantifying antigen-specific T cells, the modified RTL molecules of the invention have utility for purifying T cells for adoptive immunotherapy. For example, modified RTLs loaded with a tumor antigen may be used to purify tumor-antigen specific T cells from a cancer patient. These cells may then be expanded in vitro before being returned to the patient as part of an adoptive immunotherapeutic cancer treatment.

The modified RTL molecules of the invention can be used to alter the activity, phenotype, differentiation status, and/or pathogenic potential of T cells in an Ag-specific manner. Within alternate aspects of the invention, these novel reagents can be used to induce a variety of T cell transduction processes, to modulate T cell effector functions (including cytokine and proliferation responses), to induce anergy, or otherwise alter the pathogenic potential of T cells in an Ag-specific manner. In this regard, the modified RTLs of the invention display powerful and epitope-specific effects on T-cell activation resulting, as exemplified by their ability to stimulate secretion of anti-inflammatory cytokines (e.g., IL-10). When conjugated with a toxic moiety, the modified RTLs of the invention may also be used to kill T cells having a particular Ag specificity. Accordingly, the disclosed RTL molecules are useful in a wide range of both in vivo and in vitro applications.

Modified RTL molecules of the invention can be readily produced by recombinant expression in prokaryotic or eukaryotic cells, and can be purified in large quantities. Moreover, these molecules may easily be loaded with any desired peptide antigen, making production of a repertoire of MHC molecules with different T-cell specificities a simple task. These and other aspects of the invention are described in more detail herein below.

Figure 1:
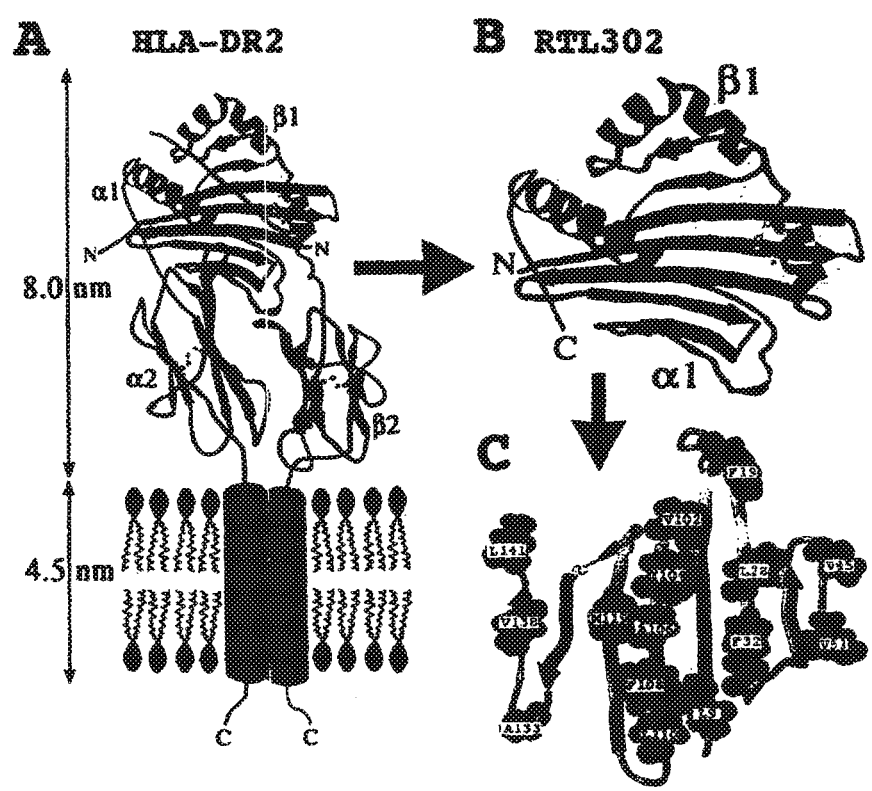
FIG. 1 shows HLA-DR2, RTL302, and the solvent accessible surface of the RTL β-sheet platform. The left panel (A) shows a scale model of an MHC class II molecule on the surface of an APC. The right panel (B) shows RTL302, a soluble single-chain molecule derived from the antigen-binding/T cell recognition domains. The lower right panel (C) shows the hydrophobic residues of the beta-sheet platform of RTL302.

The Sequence Listing is submitted as an ASCII text file in the form of the file named Sequence_Listing.txt, which was created on Dec. 15, 2015, and is 7,636 bytes, which is incorporated by reference herein.

Definitions

The term "MHC" refers to the major histocompatibility complex.

The term "RTL" or "RTLs" refers to human recombinant T cell receptor ligands.

"Ag" refers to antigen.
"APC" refers to antigen-presenting cell.
"β-ME" refers to β-mercaptoethanol.
"CD" refers to circular dichroism.
"CFA" refers to complete Freunds adjuvant.
"DLS" refers to dynamic light scattering.
"EAE" refers to experimental autoimmune encephalomyelitis.
"ELISA" refers to enzyme linked immunosorbant assay.
"HLA" refers to human leukocyte antigen.
"hu-" refers to human.
"MBP" refers to myelin basic protein.
"MHC" refers to major histocompatibility complex.
"MOG" refers to myelin oligodendrocyte glycoprotein, (murine sequence).
"MS" refers to multiple sclerosis.
"NFDM" refers to non fat dry milk.
"PBMC" refers to peripheral blood mononuclear cells.
"PBS" refers to phosphate-buffered saline.
"PCR" refers to polymerase chain reaction.
"Ptx" refers to pertussis toxin.
"RPMI" refers to growth media for cells developed at Roswell Park Memorial Institute.
"RT" refers to room temperature.
"RTL" refers to recombinant T cell receptor ligand (e.g., RTLs of G. G. Burrows, U.S. Pat. No. 6,270,772).
"S.C." refers to subcutaneous.
"SEC" refers to size exclusion chromatography.
"STR-HRP" refers to streptavidin-horseradish peroxidase conjugate.
"TCR" refers to T cell receptor.
"Tg" refers to transgenic.
"Sequence identity" refers to the similarity between amino acid sequences. Sequence identity is frequently measured in terms of percentage identity (or similarity or homology); the higher the percentage, the more similar the two sequences are. Variants of the inventive MHC domain polypeptides will possess a high degree of sequence identity when aligned using standard methods.
"MHC domain polypeptide" refers to a discrete MHC molecular domain, for example an $\alpha 1$ or $\beta 1$ domain of an MHC class II molecule.

DETAILED DESCRIPTION OF EXEMPLARY EMBODIMENTS OF THE INVENTION

Modified RTLs of the invention comprise a major histocompatibility complex (MHC) component that incorporates one or more redesigned surface structural features which have been recombinantly introduced into an otherwise native MHC polypeptide sequence. Typically, modified RTLs of the invention are rationally designed and constructed to introduce one or more amino acid changes at a solvent-exposed target site located within, or defining, a self-binding interface found in the native MHC polypeptide.

The self-binding interface that is altered in the modified RTL typically comprises one or more amino acid residue(s) that mediate(s) self-aggregation of a native MHC polypeptide, or of an "unmodified" RTL incorporating the native MHC polypeptide. Although the self-binding interface is correlated with the primary structure of the native MHC polypeptide, this interface may only appear as an aggregation-promoting surface feature when the native polypeptide is isolated from the intact MHC complex and incorporated in the context of an "unmodified" RTL.

Thus, in certain embodiments, the self-binding interface may only function as a solvent-exposed residue or motif of an unmodified RTL after the native polypeptide is isolated from one or more structural element(s) found in an intact MHC protein. In the case of exemplary MHC class II RTLs described herein (e.g., comprising linked $\beta 1$ and $\alpha 1$ domains), the native $\beta 1 \alpha 1$ structure only exhibits certain solvent-exposed, self-binding residues or motifs after removal of Ig-fold like, $\beta 2$ and $\alpha 2$ domains found in the intact MHC II complex. These same residues or motifs that mediate aggregation of unmodified $\beta 1 \alpha 1$ RTLs, are presumptively "buried" in a solvent-inaccessible conformation or otherwise "masked" (i.e., prevented from mediating self-association) in the native or progenitor MHC II complex (likely through association with the Ig-fold like, $\beta 2$ and $\alpha 2$ domains).

Certain modified RTLs of the invention include a multi-domain structure comprising selected MHC class I or MHC class II domains, or portions of multiple MHC domains that are necessary to form a minimal Ag recognition/TCR interface (i.e., which is capable of mediating Ag binding and TCR recognition). In certain embodiments, the modified RTL comprises a "minimal TCR interface", meaning a minimal subset of MHC class I or MHC class II domain residues necessary and sufficient to mediate functional peptide binding and TCR-recognition. TCR recognition requires that the modified RTL be capable of interacting with the TCR in an Ag-specific manner to elicit one or more TCR-mediated T cell responses, as described herein.

In the case of modified RTLs derived from human class II MHC molecules, the RTLs will most often comprise $\alpha 1$ and $\beta 1$ MHC polypeptide domains of an MHC class II protein, or portions thereof sufficient to provide a minimal TCR interface. These domains or subportions thereof may be covalently linked to form a single chain (Sc) MHC class II polypeptide. Such RTL polypeptides are hereinafter referred to as "$\alpha 1 \beta 1$" sc MHC class II polypeptides. Equivalent sc MHC constructs can be modeled from human MHC class I proteins, for example to form RTLs comprising $\alpha 1$ and $\alpha 2$ domains (or portions thereof sufficient to provide a minimal TCR interface) of a class I MHC protein, wherein the RTL is optionally "empty" or associated with an Ag comprising a CD8+ T cell epitope.

RTL constructs comprising sc MHC components have been shown to be widely useful for such applications as preventing and treating Ag-induced autoimmune disease responses in mammalian model subjects predictive of autoimmune disease therapeutic activity in humans (Burrows et al., J. Immunol. 161:5987, 1998; Burrows et al., J. Immunol. 164:6366, 2000). In other aspects, these types of RTLs have been demonstrated to inhibit T cell activation and induce anti-inflammatory cytokine (e.g., IL-10) secretion in human DR2-restricted T cell clones specific for MBP-85-95 or BCR-ABL b3a2 peptide (CABL) (Burrows et al., J. Immunol. 167:4386, 2001; Chang et al., J. Biol. Chem. 276:24170, 2001).

Additional RTL constructs have been designed and tested by inventors in the instant application, which include a MOG-35-55/DR2 construct (VG312) shown to potently inhibit autoimmune responses and lead to immunological tolerance to the encephalitogenic MOG-35-55 peptide and reverse clinical and histological signs of EAE (Vandenbark et al., J. Immunol. 171: 127-33, 2003). Numerous additional RTL constructs that are useful for modulating T cell immune responses and can be employed within the invention are available for use within the methods and compositions of the invention (see, e.g., U.S. Pat. No. 6,270,772, issued Aug. 7, 2001; U.S. Provisional Patent Application No. 60/064,552, filed Sep. 16, 1997; U.S. Provisional Patent Application No. 60/064,555, filed Oct. 10, 1997; U.S. Provisional Patent Application No. 60/200,942, filed May 1, 2000; U.S. Provisional Patent Application 60/500,660 entitled MONOMERIC RECOMBINANT MHC MOLECULES USEFUL FOR MANIPULATION OF ANTIGEN-SPECIFIC T-CELLS, filed by Burrows et al. on Sep. 5, 2003; U.S. patent application Ser. No. 09/153,586; filed May 1, 2001; U.S. patent application Ser. No. 09/847,172; filed May 1, 2001; and U.S. patent application Ser. No. 09/858,580; filed May 15, 2001, each incorporated herein by reference).

To evaluate the biological function and mechanisms of action of modified RTLs of the invention, antigen-specific T cells hearing cognate TCRs have been used as target T cells for various assays (see, e.g., Burrows et al., *J. Immunol.* 167:4386, 2001). More recently, inventors in the current application have provided novel T cell hybridomas that are uniquely adapted for use in screens and assays to identify and characterize RTL structure and function (see, e.g., U.S. Provisional Patent Application No. 60/586,433, filed July 7; and Chou et al., *J. Neurosci. Res.* 77: 670-680, 2004). To practice these aspects of the invention, T cell hybrids are constructed and selected that display an Ag-specific, TCR-mediated proliferative response following contact of the hybrid with a cognate Ag and APCs. This proliferative response of T hybrids can in turn be detectably inhibited or stimulated by contacting the T cell hybrid with a modified RTL of interest, which yields a modified, Ag-specific, TCR-mediated proliferation response of the hybrid. The modified proliferation response of the hybrid cell accurately and reproducibly indicates a presence, quantity, and/or activity level of the modified RTL in contact with the T cell hybrid.

The MHC component of the RTL may be provided as an "empty" RTL, or be associated by non-covalent binding or covalent linkage to a selected peptide Ag. Typically, the peptide Ag comprises one or more antigenic determinant(s) of an autoantigenic protein, for example one or more CD4+ T cell immunodominant epitope(s) associated with a selected autoimmune disease (e.g., an immunodominant epitope of myelin basic protein (MBP) or myelin oligodendrocyte protein (MOG) implicated in MS).

Within certain embodiments of the invention, an isolated, modified recombinant RTL which has a reduced potential for aggregation in solution comprises an "MHC component" in the form of a single chain (sc) polypeptide that includes multiple, covalently-linked MHC domain elements. These domain elements are typically selected from a) $\alpha 1$ and $\beta 1$ domains of an MHC class II polypeptide, or portions thereof comprising an Ag-binding pocket/T cell receptor (TCR) interface; or b) $\alpha 1$ and $\alpha 2$ domains of an MHC class I polypeptide, or portions thereof comprising an Ag-binding pocket/TCR interface. The MHC component of the RTL is modified by one or more amino acid substitution(s), addition(s), deletion(s), or rearrangement(s) at a target site corresponding to a "self-binding interface" identified in a native MHC polypeptide component of an unmodified RTL. The modified RTL modified exhibits a markedly reduced propensity for aggregation in solution compared to aggregation exhibited by an unmodified, control RTL having the same fundamental MHC component structure, but incorporating the native MHC polypeptide defining the self-binding interface.

As used herein, "native MHC polypeptide" refers to intact, naturally-occurring MHC polypeptides, as well as to engineered or synthetic fragments, domains, conjugates, or other derivatives of MHC polypeptides that have an identical or highly conserved amino acid sequence compared to an aligned sequence in the naturally-occurring MHC polypeptide (e.g., marked by 85%, 90%, 95% or greater amino acid identity over an aligned stretch of corresponding residues. The "native MHC polypeptide" having the self-associating interface will often be an MHC polypeptide domain incorporated within an unmodified RTL, and the self-associating interface may only be present in such a context, as opposed to when the native MHC polypeptide is present in a fully intact, native MHC protein (e.g., in a heterodimeric MHC class II protein complex).

Thus, in the case of MHC class II RTLs, removal of the $\beta 2$ and $\alpha 2$ domains to create a smaller, more useful (e.g., $\beta 1\alpha 1$) domain structure for the RTL (comprising a minimal TCR interface) results in "unmasking" (i.e., rendering solvent-exposed) certain self-binding residues or motifs that comprise target sites for RTL modification according to the invention. These unmasked residues or motifs can be readily altered, for example by site-directed mutagenesis, to reduce or eliminate aggregation and render the RTL as a more highly monodisperse reagent in aqueous solution.

To evaluate the extent of monodispersal of these modified RTLs, an unmodified or "control" RTL may be employed which has the same basic polypeptide construction as the modified RTL, but features the native MHC polypeptide sequence (having one or more amino acid residues or motifs comprising the self-binding interface and defining a solvent-exposed target site for the modification when the native polypeptide is incorporated in the RTL).

The modified RTLs of the invention yield an increased percentage of monodisperse molecules in solution compared to a corresponding, unmodified RTL (i.e., comprising the native MHC polypeptide and bearing the unmodified, self-binding interface). In certain embodiments, the percentage of unmodified RTL present as a monodisperse species in aqueous solution may be as low as 1%, more typically 5-10% or less of total RTL protein, with the balance of the unmodified RTL being found in the form of higher-order aggregates. In contrast, modified RTLs of the present invention will yield at least 10%-20% monodisperse species in solution. In other embodiments, the percentage of monomeric species in solution will range from 25%-40%, often 50%-75%, up to 85%, 90%, 95% or greater of the total RTL present, with a commensurate reduction in the percentage of aggregate RTL species compared to quantities observed for the corresponding, unmodified RTLs under comparable conditions.

The self-binding interface that is altered in the MHC polypeptide to form the modified RTL may comprise single or multiple amino acid residues, or a defined region, domain, or motif of the MHC polypeptide, which is characterized by an ability to mediate self-binding or self-association of the MHC polypeptide and/or RTL. As used herein, "self-binding" and "self-association" refers to any intermolecular binding or association that promotes aggregation of the MHC polypeptide or RTL in a physiologically-compatible solution, such as water, saline, or serum.

As noted above, MHC class II molecules comprise non-covalently associated, $\alpha$- and $\beta$-polypeptide chains. The $\alpha$-chain comprises two distinct domains termed $\alpha 1$ and $\alpha 2$. The $\beta$-chain also comprises two domains, $\beta 1$ and $\beta 2$. The peptide binding pocket of MHC class II molecules is formed by interaction of the $\alpha 1$ and $\beta 1$ domains. Peptides from processed antigen bind to MHC molecules in the membrane distal pocket formed by the β1 and α1 domains (Brown et al., 1993; Stern et al., 1994). Structural analysis of human MHC class II/peptide complexes (Brown et al., *Nature* 364:33-39, 1993; Stern et al., *Nature* 368:215, 1994) demonstrate that side chains of bound peptide interact with "pockets" comprised of polymorphic residues within the class II binding groove. The bound peptides have class II allele-specific motifs, characterized by strong preferences for specific amino acids at positions that anchor the peptide to the binding pocket and a wide tolerance for a variety of different amino acids at other positions (Stern et al., *Nature* 368:215, 1994; Rammensee et al., *Immunogenetics* 41: 178, 1995). Based on these properties, natural populations of MHC class II molecules are highly heterogeneous. A given allele of class II molecules on the surface of a cell has the ability to bind and present over 2000 different peptides. In addition, bound peptides dissociate from class II molecules with very slow rate constants. Thus, it has been difficult to generate or obtain homogeneous populations of class II molecules bound to specific antigenic peptides.

The α2 and β2 domains of class II molecules comprise distinct, trans-membrane Ig-fold like domains that anchor the α- and β-chains into the membrane of the APC. In addition, the α2 domain is reported to contribute to ordered oligomerization during T cell activation (Konig et al., *J. Exp. Med.* 182:778-787, 1995), while the β2 domain is reported to contain a CD4 binding site that co-ligates CD4 when the MHC-antigen complex interacts with the TCR αβ heterodimer (Fleury et al., *Cell* 66:1037-1049, 1991; Cammarota et al., *Nature* 356:799-801, 1992; König et al., *Nature* 356: 796-798, 1992; Huang et al., *J. Immunol.* 158:216-225, 1997).

RTLs modeled after MHC class II molecules for use within the invention typically comprise small (e.g., approximately 200 amino acid residues) molecules comprising all or portions of the α1 and β1 domains of human and non-human MHC class II molecules, which are typically genetically linked into a single polypeptide chain (with and without covalently coupled antigenic peptide). Exemplary MHC class II-derived "β1α1" molecules retain the biochemical properties required for peptide binding and TCR engagement (including TCR binding and/or partial or complete TCR activation). This provides for ready production of large amounts of the engineered RTL for structural characterization and immunotherapeutic applications. The MHC component of MHC class II RTLs comprise a minimal, Ag-binding/T cell recognition interface, which may comprise all or portions of the MHC class II α1 and β1 domains of a selected MHC class II molecule. These RTLs are designed using the structural backbone of MHC class II molecules as a template. Structural characterization of RTLs using circular dichroism indicates that these molecules retain an antiparallel β-sheet platform and antiparallel α-helices observed in the corresponding, native (i.e., wild-type sequence) MHC class II heterodimer. These RTLs also exhibit a cooperative two-state thermal folding-unfolding transition. When the RTL is covalently linked with Ag peptide they often show increased stability to thermal unfolding relative to empty RTL molecules.

In exemplary embodiments of the invention, RTL design is rationally based on crystallographic coordinates of human HLA-DR, HLA-DQ, and/or HLA-DP proteins, or of a non-human (e.g., murine or rat) MHC class II protein. In this context, exemplary RTLs have been designed based on crystallographic data for HLA DR1 (PDB accession code 1AQD), which design parameters have been further clarified, for example, by sequence alignment with other MHC class II molecules from rat, human and mouse species. The program Sybyl (Tripos Associates, St Louis, Mo.) is an exemplary design tool that can be used to generate graphic images using, for example, an O2 workstation (Silicon Graphics, Mountain View, Calif.) and coordinates obtained for HLA-DR, HLA-DQ, and/or HLA-DP molecules. Extensive crystallographic characterizations are provided for these and other MHC class II proteins deposited in the Brookhaven Protein Data Bank (Brookhaven National Laboratories, Upton, N.Y.).

Detailed description of HLA-DR crystal structures for use in designing and constructing modified RTLs of the invention is provided, for example, in Ghosh et al., *Nature* 378:457, 1995; Stern et al., *Nature* 368:215, 1994; Murthy et al., *Structure* 5:1385, 1997; Bolin et al., *J. Med. Chem.* 43:2135, 2000; Li et al., *J. Mol. Biol.* 304:177, 2000; Hennecke et al., *Embo J.* 19:5611, 2000; Li et al., *Immunity* 14:93, 2001; Lang et al., *Nat. Immunol.* 3:940, 2002; Sundberg et al., *J. Mol. Biol.* 319:449, 2002; Zavala-Ruiz et al., *J. Biol. Chem.* 278:44904, 2003; Sundberg et al., *Structure* 11:1151, 2003. Detailed description of HLA-DQ crystal structures is provided, for example, in Sundberg et al., *Nat. Struct. Biol.* 6:123, 1999; Li et al., *Nat. Immunol.* 2:501, 2001; and Siebold et al., *Proc. Nat. Acad. Sci. USA* 101: 1999, 2004. Detailed description of a murine MHC I-A$^U$ molecule is provided, for example, in He et al., *Immunity* 17:83, 2002. Detailed description of a murine MHC class II I-Ad molecule is provided, for example, in Scott et al., *Immunity* 8:319, 1998. Detailed description of a murine MHC class II I-Ak molecule is provided, for example, in Reinherz et al., *Science* 286:1913, 1999, and Miley et al., *J. Immunol.* 166:3345, 2001. Detailed description of a murine MHC allele I-A(G7) is provided, for example, in corner et al., *Science* 288:501, 2000. Detailed description of a murine MHC class II H2-M molecule is provided, for example, in Fremont et al., *Immunity* 9:385, 1998. Detailed description of a murine MHC class II H2-Ieβ molecule is provided, for example, in Krosgaard et al., *Mol. Cell* 12:1367, 2003; Detailed description of a murine class II Mhc I-Ab molecule is provided, for example, in Zhu et al., *J. Mol. Biol.* 326:1157, 2003. HLA-DP Lawrance et al., Nucleic Acids Res. 1985 Oct. 25; 13(20): 7515-7528

Structure-based homology modeling is based on refined crystallographic coordinates of one or more MHC class I or class II molecule(s), for example, a human DR molecule and a murine I-E$^k$ molecule. In one exemplary study by Burrows and colleagues (*Protein Engineering* 12:771-778, 1999), the primary sequences of rat, human and mouse MHC class II were aligned, from which it was determined that 76 of 256 α-chain amino acids were identical (30%), and 93 of the 265 β-chain amino acids were identical (35%). Of particular interest, the primary sequence location of disulfide-bonding cysteines was conserved in all three specks, and the backbone traces of the solved structures showed strong homology when superimposed, implying an evolutionarily conserved structural motif, with side-chain substitutions designed to allow differential antigenic-peptide binding in the peptide-binding groove.

Further analysis of MHC class I and class II molecules for constructing modified RTLs of the invention focuses on the "exposed" (i.e., solvent accessible) surface of the β-sheet platform/anti-parallel α-helix that comprise the domain(s) involved in peptide binding and T cell recognition. In the case of MHC class II molecules, the α1 and β1 domains exhibit an extensive hydrogen-bonding network and a tightly packed and "buried" (i.e., solvent inaccessible)

hydrophobic core. This tertiary structure is similar to molecular features that confer structural integrity and thermodynamic stability to the α-helix/β-sheet scaffold characteristic of scorpion toxins, which therefore present yet additional structural indicia for guiding rational design of modified RTLs herein (see, e.g., Zhao et al., *J. Mol. Biol.* 227:239, 1992; Housset, *J. Biol.* 238:88-91, 1994; Zinn-Justin et al., Biochemistry 35:8535-8543, 1996).

From these and other comparative data sources, crystals of native MHC class II molecules have been found to contain a number of water molecules between a membrane proximal surface of the β-sheet platform in and a membrane distal surfaces of the α2 and β2 Ig-fold domains. Calculations regarding the surface area of interaction between domains can be quantified by creating a molecular surface, for example for the β1α1 and α2β2 Ig-fold domains of an MHC molecule, using an algorithm such as that described by Connolly (*Biopolymers* 25:1229-1247, 1986) and using crystallographic coordinates (e.g., as provided for various MHC class II molecules in the Brookhaven Protein Data Base.

For an exemplary, human DR1 MHC class II molecule (PDB accession numbers 1SEB, 1AQD), surface areas of the β1α1 and α2β2-Ig-fold domains were calculated independently, defined by accessibility to a probe of radius 0.14 nm, about the size of a water molecule (Burrows et al., *Protein Engineering* 12:771-778, 1999). The surface area of the MHC class II αβ-heterodimer was 156 $nm^2$, while that of the β1α1 construct was 81 $nm^2$ and the α1β2-Ig-fold domains was 90 $nm^2$. Approximately 15 $nm^2$ (18.5%) of the β1α1 surface was found to be buried by the interface with the Ig-fold domains in the MHC class II αβ-heterodimer. Side-chain interactions between the β1α1-peptide binding and Ig-fold domains (α2 and β2) were analyzed and shown to be dominated by polar interactions with hydrophobic interactions potentially serving as a "lubricant" in a highly flexible "ball and socket" type inter face.

These and related modeling studies suggest that the antigen binding domain of MHC class II molecules remain stable in the absence of the α2 and β2 Ig-fold domains, and this production has been born out for production of numerous, exemplary RTLs comprising an MHC class II "α1β1" architecture. Related findings were described by Burrows et al. (*J. Immunol.* 161:5987-5996, 1998) for an "empty" β1α1 RTL, and four α1β1 RTL constructs with covalently coupled rat and guinea pig antigenic peptides: β1 1-Rt-MBP-72-89, β1 1-Gp-MBP-72-89, β1 1-Gp-MBP-55-69 and β1 1-Rt-CM-2. For each of these constructs, the presence of native disulfide bonds between cysteines (β15 and β79) was demonstrated by gel shift assay with or without the reducing agent β-mercaptoethanol (β-ME). In the absence of β-ME, disulfide bonds are retained and the RTL proteins typically move through acrylamide gels faster due to their more compact structure. These data, along with immunological findings using MHC class II-specific monoclonal antibodies to label conserved epitopes on the RTLs generally affirm the conformational integrity of RTL molecules compared to their native MHC II counterparts (Burrows et al., 1998, supra; Chang et al., *J. Biol. Chem.* 276:24170-14176, 2001; Vandenbark et al., *J. Immunol.* 171:127-133, 2003). Similarly, circular dichroism (CD) studies of MHC class II-derived RTLs reveal that β1α1 molecules have highly ordered secondary structures. Typically, RTLs of this general construction shared the β-sheet platform/anti-parallel α-helix secondary structure common to all class II antigen binding domains. In this context, β1α1 molecules have been found to contain, for example, approximately 30% α-helix, 15% β-strand, 26% β-turn and 29% random coil structures. RTLs covalently bound to Ag peptide (e.g., MBP-72-89, and CM-2) show similar, although not identical, secondary structural features. Thermal denaturation studies reveal a high degree of cooperativity and stability of RTL molecules, and the biological integrity of these molecules has been demonstrated in numerous contexts, including by the ability of selected RTLs to detect and inhibit rat encephalitogenic T cells and treat experimental autoimmune encephalomyelitis.

According to these and related findings provided herein (or described in the cited references which are collectively incorporated herein for all disclosure purposes), RTL constructs of the invention, with or without an associated antigenic peptide, retain structural and conformational integrity consistent with that of refolded native MHC molecules. This general finding is exemplified by results for soluble single-chain RTL molecules derived from the antigen-binding/TCR interface comprised of all or portions of the MHC class II β1 and α1 domains. In more detailed embodiments, these exemplary MHC class II RTLs lack the α2 domain and β2 domain of the corresponding, native MHC class II protein, and also typically exclude the transmembrane and infra-cytoplasmic sequences found in the native MHC II protein. The reduced size and complexity of these RTL constructs, exemplified by the "β1α1" MHC II RTL constructs, provide for ready and predictable expression and purification of the RTL molecules from bacterial inclusion bodies in high yield (e.g., up to 15-30 mg/1 cell culture or greater yield).

In native MHC class II molecules, the Ag peptide binding/T cell recognition domain is formed by well-defined portions of the α1 and β1 domains of the α and β polypeptides which fold together to form a tertiary structure, most simply described as a β-sheet platform upon which two anti-parallel helical segments interact to feint an antigen-binding groove. A similar structure is formed by a single exon encoding the α1 and α2 domains of MHC class I molecules, with the exception that the peptide-binding groove of MHC class II is open-ended, allowing the engineering of single-exon constructs that encode the peptide binding/T cell recognition domain and an antigenic peptide ligand.

As exemplified herein for MHC class II proteins, modeling studies highlighted important features regarding the interface between the β1α1 and α2β2-Ig-fold domains that have proven critical for designing modified, monodisperse RTLs of the invention. The α1 and β1 domains show an extensive hydrogen-bonding network and a tightly packed and "buried" (i.e., solvent inaccessible) hydrophobic core. The β1α1 portion of MHC class II proteins may have the ability to move as a single entity independent from the α2β2-Ig-fold 'platform'. Besides evidence of a high degree of mobility in the side-chains that make up the linker regions between these two domains, crystals of MHC class II I-Ek contained a number of water molecules within this interface (Jardetzky et al., *Nature* 368: 711-715, 1994; Fremont et al., *Science* 272:1001-1004, 1996; Murthy et al., *Structure* 5:1385, 1997). The interface between the β1α1 and α2β2-Ig-fold domains appears to be dominated by polar interactions, with hydrophobic residues likely serving as a 'lubricant' in a highly flexible 'ball and socket' type interface. Flexibility at this interface may be required for freedom of movement within the α1 and β1 domains for binding/exchange of peptide antigen. Alternatively or in combination, this interaction surface may play a role in communicating information about the MHC class II peptide molecular interaction with TCRs back to the APC.

Following these rational design guidelines and parameters, the instant inventors have successfully engineered modified, monodisperse derivatives of single-chain human RTLs comprising peptide binding/TCR recognition portions of human MHC class II molecules (e.g., as exemplified by a HLA-DR2b (DRA*0101/DRB1*1501). Unmodified RTLs constructed from the α1 and β1 domains of this exemplary MHC class II molecule retained biological activity, but formed undesired, higher order aggregates in solution.

To resolve the problem of aggregation in this exemplary, unmodified RTL, site-directed mutagenesis was directed towards replacement of hydrophobic residues with polar (e.g., serine) or charged (e.g., aspartic acid) residues to modify the β-sheet platform of the DR2-derived RTLs. According to this rational design procedure, novel RTL variants were obtained that were determined to be predominantly monomeric in solution. Size exclusion chromatography and dynamic light scattering demonstrated that the novel modified RTLs were monomeric in solution, and structural characterization using circular dichroism demonstrated a highly ordered secondary structure of the RTLs.

Peptide binding to these "empty", modified RTLs was quantified using biotinylated peptides, and functional studies showed that the modified RTLs containing covalently tethered peptides were able to inhibit antigen-specific T cell proliferation in vitro, as well as suppress experimental autoimmune encephalomyelitis in vivo. These studies demonstrated that RTLs encoding the Ag-binding/TCR recognition domain of MHC class II molecules are innately very robust structures. Despite modification of the RTLs as described herein, comprising site-directed mutations that modified the β-sheet platform of the RTL, these molecules retained potent biological activity separate from the Ig-fold domains of the progenitor class II structure, and exhibited a novel and surprising reduction in aggregation in aqueous solutions. Modified RTLs having these and other redesigned surface features and monodispersal characteristics retained the ability to bind Ag-peptides, inhibit T cell proliferation in an Ag-specific manner, and treat, inter alia, autoimmune disease in vivo.

Additional modifications apart from the foregoing surface feature modifications can be introduced into modified RTLs of the invention, including particularly minor modifications in amino acid sequence(s) of the MHC component of the RTL that are likely to yield little or no change in activity of the derivative or "variant" RTL molecule. Preferred variants of non-aggregating MHC domain polypeptides comprising a modified RTLs are typically characterized by possession of at least 50% sequence identity counted over the full length alignment with the amino acid sequence of a particular non-aggregating MHC domain polypeptide using the NCBI Blast 2.0, gapped blastp set to default parameters. Proteins with even greater similarity to the reference sequences will show increasing percentage identities when assessed by this method, such as at least 60%, at least 65%, at least 70%, at least 75%, at least 80%, at least 90% or at least 95% sequence identity. When less than the entire sequence is being compared for sequence identity, variants will typically possess at least 75% sequence identity over short windows of 10-20 amino acids, and may possess sequence identities of at least 85% or at least 90% or 95% depending on their similarity to the reference sequence. Methods for determining sequence identity over such short windows are known in the art as described above. Variants of modified RTLs comprising non-aggregating MHC domain polypeptides also retain the biological activity of the non-variant, modified RTL. For the purposes of this invention, that activity may be conveniently assessed by incorporating the variation in the appropriate MHC component of a modified RTL (e.g., a β1α1 MHC component) and determining the ability of the resulting RTL/Ag complex to inhibit Ag-specific T-cell proliferation in vitro, as described herein.

Rationally Designed Mutations Converted Complexes of Human Recombinant T Cell Receptor Ligands into Monomers that Retain Biological Activity Applicant's herein demonstrate and disclose that the potent biological activity of particular RTLs (Burrows et al., *J. Immunol.* 167:4386-95; 2001; Wang et al., *The Journal of Immunology*, 2003; Vandenbark et al., *Journal of Immunology*, 2003) was retained when produced in a monomeric form, with the ability to inhibit T cell proliferation in vitro. Extremely important from a clinical perspective, the monomeric form is able to reverse clinical signs of EAE and induce long-term T cell tolerance against the encephalitogenic, DR2-restricted, MOG-35-55 peptide in Tg mice that uniquely express this multiple sclerosis-associated HLA-DR2 allele.

Applicant's earlier studies had demonstrated that immunization of Tg-DR2 mice with MOG-35-55 peptide induced strong T cell responses, perivascular spinal cord lesions with demyelination, and severe chronic signs of EAE, as well as anti-MOG antibodies that were apparently not involved in either disease or tolerance induction (Vandenbark et al., *Journal of Immunology*, 2003).

As disclosed herein, treatment of the Tg-DR2 mice after onset of clinical EAE with an 8-day course of daily i.v. injections of 33 μg RTL342 reversed disease progression to baseline levels and maintained reduced clinical activity even after cessation of further injections. Treatment with control RTL303 containing covalently tethered MBP-87-99 did not inhibit EAE or affect T cell responses to MOG-35-55 peptide, demonstrating antigen specificity.

Significantly, the applicant's teachings are the first to document that monomeric RTLs have such potent clinical activity, and that the molecules are suitable for evaluation for use in human clinical trials for treatment of multiple sclerosis.

The peptide binding/TCR recognition domain of MHC class II from which RTLs are derived contain a complex mixture of alpha-helix and beta-sheet secondary structure, as well as a highly conserved post-translational modification, a disulfide bond between cysteines at position 16 and 80 (RTL302 numbering). These molecules are small enough to systematically dissect with currently available technology, yet complex enough that successful engineering of other MHC molecules and derivatives, comprehensive of HLA-DR, HLA-DQ, and HLA-DP molecules and derivatives, will require application of the novel protein engineering findings and concepts disclosed herein.

MHC class II molecules have (at least) three clearly defined biochemical "functions" that can be used to evaluate and quantify the retention of a specific three-dimensional fold derived from the primary sequence: Ag-peptide binding, TCR binding and CD4 binding. Without being bound by theory, applicant's hypothesized that these functions have been encoded and superimposed onto the primary sequence of MHC class II, and that some of these functions can be separated experimentally for evaluation using protein engineering (Burrows et al., *Protein Engineering* 12:771-78, 1999; Chang et al., *J. Biol. Chem.* 276:24170-76, 2001).

For purposes of the present invention, it is desirable to retain two key biochemical functions: the ability to specifically bind Ag-peptides; and the ability to bind the αβ heterodimer chains of the TCR. Retention of these key features allows discernment of the minimal interaction interface with the T cell that still initiates a throughput information signal (Wang et al., *The Journal of Immunology*, 2003), allowing engineering a molecular system for controlling CD4$^+$ T cells in an Ag-specific manner.

While HLA-DR2-derived RTLs with the wild-type sequence retained these two key biological activities (Vandenbark et al., *Journal of Immunology*, 2003), they tended to form higher-order structures (Burrows et al., *J. Immunol* 167:4386-95, 2001) that could not be completely eliminated by manipulating solvent conditions. For example, an optimal yield of monodisperse monomeric RTL302 of almost 20% was obtained by decreasing the concentration of purified RTL302 protein to 0.1 mg/ml for the final folding step, and changing buffers from phosphate-buffered saline to Tris. However, concentrating purified RTL302 monomer above 0.2 mg/ml caused the molecules to repartition back into a mixture of monomer and aggregate, an equilibrium that was concentration dependent. According to the present invention, aggregation of HLA-DR2 derived RTLs is specific to certain portions of the DR2-derived RTL sequence.

A 2.6 angstrom resolution crystal structure of HLA-DR2 with bound Ag-peptide MBP-85-99 (PDB accession 1BX2; (Smith et al., *J. Exp. Med.* 188:1511-20, 1998), provided sufficient data to permit analysis herein of the membrane-proximal surface of the β-sheet platform and the membrane distal surfaces of the α2 and β2 Ig-fold domains, specifically identifying features that contribute to higher-order structures or aggregation when the subject MHC II domains are incorporated in an unmodified RTL. Specifically, according to the present invention, the β-sheet platform buried in the progenitor HLA-DR2 molecule defines the bottom of the RTLs, and contains a number of hydrophobic residues that are typically found buried within a protein structure rather than being solvent exposed.

The propensity of different amino acid residues to be present in β-sheet structures has been intensively investigated (Minor et al., *Nature* 367:660-63, 1994; Pokkuluri et al., *Protein Science* 11:1687-94, 2002; Street et al., *Proc. Natl. Acad. Sci. USA* 96:9074-76; 1999; Chou et al., *Biochemistry* 13:211-22, 1973; Smith et al., *Biochemistry* 33:5510-17, 1994; Finkelstein, *Protein Engineering* 8:207-09, 1995), as part of an overall goal of understanding the rules that dictate secondary structure stability and formation. The body of work available has defined the markedly high preference in β-sheets for the β-branched amino acids isoleucine, valine, and threonine, as well as aromatic amino acid residues phenylalanine and tyrosine.

According to the present invention, desired surface modification of an RTL comprising an MHC class II component to yield much less aggregation prone form can be achieved, for example, by replacement of one or more hydrophobic residues identified in the β-sheet platform of the MHC component with non-hydrophobic residues, for example polar or charged residues. Modified RTL constructs exemplifying this aspect of the invention were constructed by replacing one or more target, hydrophobic residues identified in the β-sheet platform of an HLA-DR2 component of RTL 302 with one or more exemplary polar (e.g., serine) residue(s) and, alternatively exemplary charged (e.g., aspartate) residue(s). FIG. 1 depicts the targeted β-sheet platform residues for modification. Initially, a central core portion of the β-sheet platform was targeted for modification, comprising V102, I104, A106, F108, and L110 (shown from top to bottom in FIG. 1C). These residues were changed by site-directed mutagenesis, individually, or in various multiple-residue combinations to either a serine, or aspartate residue(s).

Individual changes of these hydrophobic residues to a different, polar or charged residue, generally yielded detectable reductions in aggregation of the modified RTL. The more hydrophobic residues that were changed, either to a polar or charged residue, the greater the expected reduction in aggregation potential. When all five of the indicated, core β-sheet platform target residues were changed, a substantial conversion of the RTLs to a more monodisperse form was observed. When all five core target residues were changed to a serine residue, approximately 15% of the modified RTLs were rendered monomeric in solution. When all five core target residues (comprising an exemplary, self-binding "motif" of the DR molecule) were changed to apartate residues, substantially all of the modified RTLs were observed in a monodisperse form in solution (see below). As illustrated in FIG. 1C, additional hydrophobic target residues are available for modification to alter self-binding characteristics of the β-sheet platform portion of DR2 molecules incorporated in RTLs. In reference to FIG. 1C, the left arm of the diagrammed β-sheet platform includes a separate "motif" of three noted hydrophobic residues (top to bottom), L141, V138, and A133 that will serve as useful targets for individual or collective modification (e.g., by site directed amino acid deletion or substitution) to remove the hydrophobic residue(s) or alter the target residue(s) to a non-hydrophobic (e.g., polar, or charged) residue. Also in reference to FIG. 1C, several target hydrophobic residues are marked to the right of the core β-sheet motif, including L9, F19, L28, F32, V45, and V51, which may be regarded as one or more additional, self-binding or self-associating target "motifs" for RTL modification. Any one or combination of these residues may be targeted for modification to remove the hydrophobic residue(s) or alter the target residue(s) to a non-hydrophobic residue, with the expectation of yielding further benefits with regard to diminishing aggregation potential of the modified RTL.

RTL modification typically involves amino acid substitution or deletion at target sites for mutagenesis comprising a self-binding interface (comprised of one or more amino acid residues, or a self-binding motif formed of several target residues). Within exemplary embodiments directed toward production of modified RTLs that comprise MHC class II RTL components, targeted residues for modification typically comprise hydrophobic residues or motifs, for example valine, leucine, isoleucine, alanine, phenylalanine, tyrosine, and tryptophan. These and other target residues may be advantageously deleted, or alternatively substituted for any non-hydrophobic amino acid. Suitable substituent amino acids for generating desired RTL modifications can include amino acids having aliphatic-hydroxyl side chains, such as serine and threonine; amino acids having amide-containing side chains, such as asparagine and glutamine; amino acids having aromatic side chains, such as phenylalanine, tyrosine, and tryptophan; and amino acids having basic side chains, such as lysine, arginine, and histidine.

Figure 6:
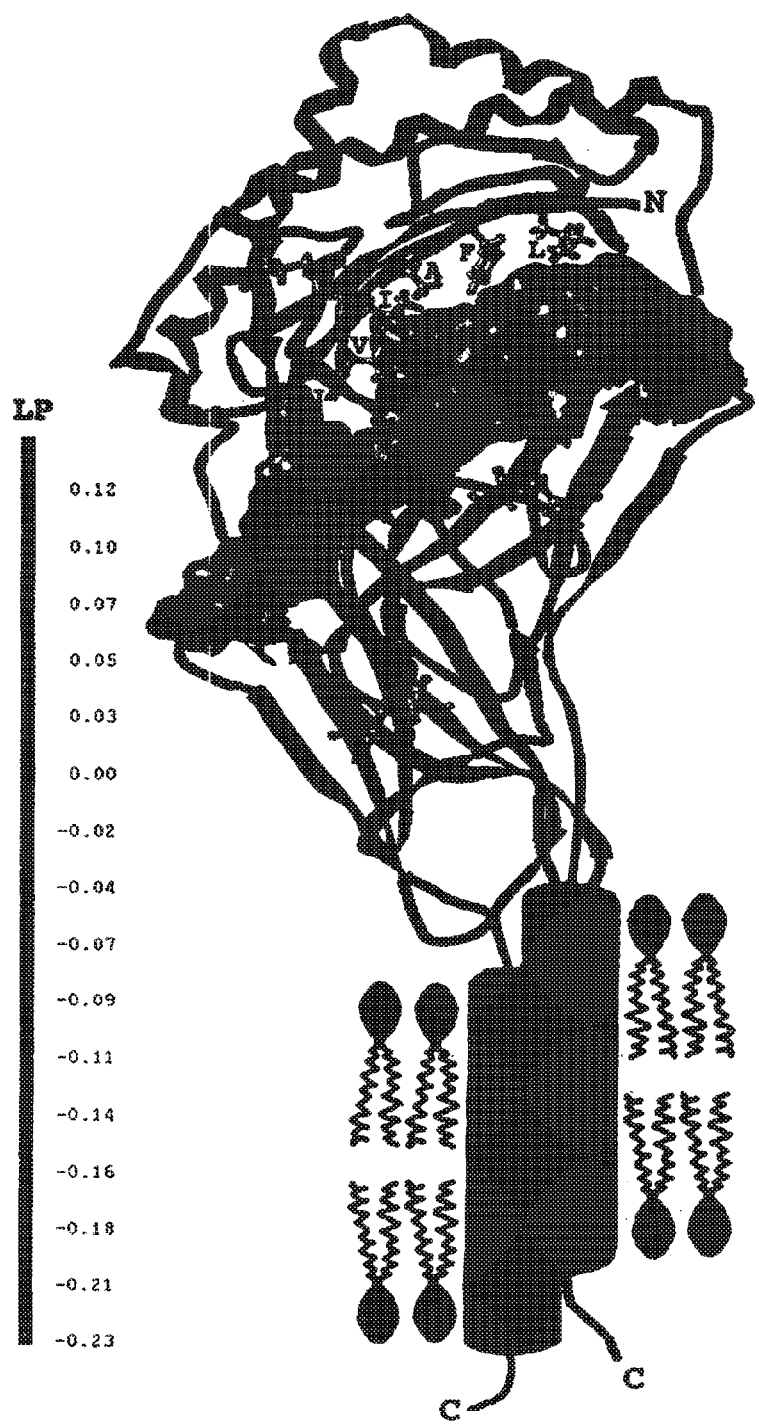
FIG. 6 shows the interaction surface between the α1β1 peptide binding/T cell recognition domain and the α2β2-Ig-fold domains of HLA-DR2. The interaction surface between the α1β1 peptide binding/T cell recognition domain and the α2β2-Ig-fold domains was modeled and refined using the high resolution human class II DR2 structure 1 BX2 (Smith et al., *J. Exp. Med.* 188:1511-20, 1998). The transmembrane domains are shown schematically as 0.5 nm cylinders. The amino and carboxyl termini of MHC class II are labeled N, C, respectively. Cysteines are rendered as ball-and-stick, as are the five residues V102, I104, A106, F108, LIIO (1BX2 numbering). The interaction surface (4 angstrom interface) between the Ig-fold domains and the peptide binding/T cell recognition domain is colored by lipophilic potential (LP). Water molecules within this interface in the 1BX2 crystal structure are shown as spheres.

The findings presented herein validate the rational design approach of the current invention for modifying a diverse array of RTLs comprising various MHC components, including MHC class I and MHC class II components, to diminish the propensity of the modified RTL for aggregation in solution. These concepts are clearly applicable to all types of MHC class II molecules, which exhibit a high degree of conservation of higher order structure, including particularly in the β-sheet platform portion of the molecule that is solvent-exposed through production of RTLs (e.g., comprising β1α1 MHC class II sc polypeptide) The beta strand of the HLA-DR2 component successfully modified in exemplary RTLs herein defines an extended, central strand within the progenitor HLA-DR2 molecule (FIG. 6). The 2.6 angstrom resolution crystal structure of HLA-DR2 with bound Ag-peptide MBP-85-99 (PDB accession 1BX2; (Smith et al., J. Exp. Med. 188:1511-20, 1998)), permitted analysis herein of the membrane-proximal surface of the β-sheet platform and the membrane distal surfaces of the α2 and β2 Ig-fold domains, specifically identifying features that contributed to higher-order structures or aggregation. Specifically, according to the present invention, the beta-sheet platform buried in the progenitor HLA-DR2 molecule defines the bottom of the RTLs, and contains a number of hydrophobic residues that are typically found buried within a protein structure rather than being solvent exposed.

All human HLA-DR molecules will follow closely the modification rules and expectations for rational design disclosed herein. Likewise, human HLA-DQ and HLA-DP class II molecules, and various murine, rat and other mammalian class II MHC molecules, are described and characterized sufficiently (see references cited above, which are incorporated herein) to apply the structure-function analytical rules of the invention relating to identification and modification of RTL self-binding interface residues and motifs to these related subjects within the methods and compositions of the invention.

Figure 3:
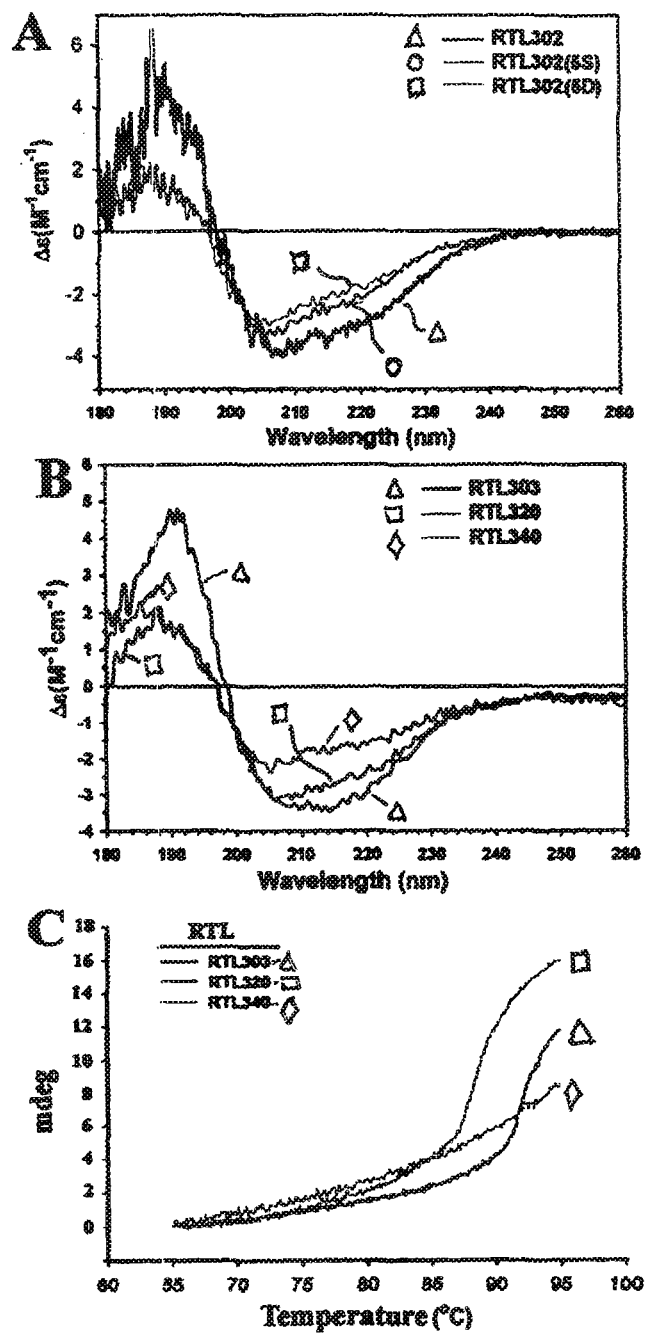
FIG. 3 shows circular dichroism (CD) spectra of modified DR2-derived RTLs. The upper panel (A) shows CD spectra of "empty" RTL302 (triangle), RTL302(5S) (circle) and RTL302(5D) (square). The middle panel (B) shows CD spectra of RTLs containing covalently tethered Ag MBP-85-99 peptide. RTL303, (triangle), RTL320 (square), and RTL340 (diamond). The lower panel (C) shows thermal denaturation curves for RTL303, RTL320 and RTL340 which reveal a high degree of cooperativity and stability.

In the case of exemplary, modified, DR2-derived RTLs, the greatest success in terms of rendering monodisperse RTL derivatives was obtained by substitution of all five β-sheet platform core hydrophobic residues with an exemplary charged residue, aspartate. Aspartate is significantly underrepresented in β-sheet regions of proteins, and the introduction herein of either five serine, or five aspartate residues on the external face of an interior strand of the β-sheet platform of RTLs had only a subtle effect on the secondary structure as quantified by circular dichroism (FIG. 3). This moderate effect was interpreted as an approximately 10% increase of anti-parallel β-strand structure upon deconvolution of the spectra (Table III).

A likely explanation for why these exemplary modified RTLs maintain the same basic fold and biological features as their counterpart, unmodified RTLs bearing the native MHC components and self-binding residues/motifs, comes from analysis of the β-sheet in the context of its functional role as an "open" platform in the overall tertiary structure of the Ag-binding/TCR recognition domain of the progenitor HLA-DR2 molecule, rather than a closed surface like an Ig-fold. The propensity of different amino acid residues to be present in β-sheet structures has been intensively investigated (Minor et al., Nature 367:660-63, 1994; Pokkuluri et al., Protein Science 11:1687-94, 2002; Street et al., Proc. Natl. Acad. Sci. USA 96:9074-76; 1999; Chou et al., Biochemistry 13:211-22, 1973; Smith et al., Biochemistry 33:5510-17, 1994; Finkelstein, Protein Engineering 8:207-09, 1995), as part of an overall goal of understanding the rules that dictate secondary structure stability and formation. The body of work available has defined the markedly high preference in β-sheets for the β-branched amino acids isoleucine, valine, and threonine, as well as aromatic amino acid residues phenylalanine and tyrosine.

To illustrate the broad applicability of the rational design principles and methods of the invention for constructing modified, monodisperse RTLs from a diverse array of MHC components, the following alignment is presented documenting homologous self-binding motifs identified within different, exemplary RTLs constructed with homologous MHC components from HLA-DR, HLA-DP, and HLA-DQ MHC class II molecules.

```
         1 ---------+---------+---------+---------+---------+---------+  60
       302 MGDTRPRFLWQPKRECHFFNGTERVRFLDRYFYNQEESVRFDSDVGEFRAVTELGRPDAE
       600 MGDTPENYLFQGRQECYAFNGTQR--FLERYIYNREEFVRFDSDVGEFRAVTELGRPDEE
       800 MRDSPEDFVYQFKGMCYFTNGTERVRLVSRSIYNREEIVRFDSDVGEFRAVTLLGLPAAE

61 ---------+---------+---------+---------+---------+---------+ 120
       302 YWNSQKDILEQARAAVDTYCRHNYGVVESFTVQRRVIKEEHVIIQAEFYLNPDQSGEFMF
       600 YWNSQKDILEEERAVPDRMCRHNYELGGPMTLQRRVIKADHVSTYAAFVQTHRPTGEFMF
       800 YWNSQKDILERKRAAVDRVCRHNYQLELRTTLQRRVEDIVADHVASYGVNLYQSYGPSGQ

121 ---------+---------+---------+---------+---------+---------+ 180
       302 DFDGDEIFHVDMAKKETVWRLEEFGRFASFEAQGALANIAVDKANLEIMTKRSNYTPITN
       600 EFDEDEMFYVDLDKKETVWHLEEFGQAFSFEAQGGLANIAILNNNLNTLIQRSNHTQATN
       800 YTHEFDGDEQFYVDLGRKETVWCLPVLRQFRGFDPQFALTNIAVLKHNLNSLIKRSNSTAATN
       Primary amino acid sequence alignment of human RTLs .
       RTL302 was derived from DR2 (DRB1*15011/DRA*0101) (31)(SEQ ID NO: 9).
       RTL600 was derived from DP2 (DPA1*0103/DPB1*0201) (SEQ ID NO: 10).
       RTL800 was derived from DQ2 (DQA1*05/DQB1*02) (SEQ ID NO: 11)
       (**Italics indicate non-native amino acid residues. Gaps in the sequences for optimal
       alignment (-) and the beta 1//alpha 1 junction (↓) are also shown.
       The conserved cysteines that form a disulfide bond are shaded.
```

The foregoing alignment maps a homologous self-binding motif identified and modified herein for an exemplary HLA-DR2 component in RTL302 in alignment with homologous target residues comprising self-binding motifs on additional RTLs constructed by the present inventors, including RTL600, comprising a DP2 MHC component, and RTL800, comprising a DQ2 MHC component. Consistent with the disclosure and teachings herein, numerous exemplary target residues of RTL600 and RTL800 are readily discerned (e.g., as matched with target DR2 residues marked by underscoring in the alignment) for modification of these additional DQ and DP MHC class II species to produce modified RTLs according to the invention.

With respect to designing modified RTLs containing an MHC class II component, FIG. 6 shows the interaction surface between the oil α1β1 peptide binding/T cell recognition domain and the α2β2-Ig-fold domains of HLA-DR2. The interaction surface between the α1β1 peptide binding/T cell recognition domain and the α2β2-Ig-fold domains was modeled and refined using the high resolution human class II DR2 structure 1BX2 (Smith et al., J. Exp. Med. 188:1511-20, 1998). The transmembrane domains are shown schematically as 0.5 nm cylinders. The amino and carboxyl termini of MHC class II are labeled N, C, respectively. Cysteines are rendered as ball-and-stick, as are the five residues V102, I104, A106, F108, L110 (1BX2 numbering). The interaction surface (4 angstrom interface) between the Ig-fold domains and the peptide binding/T cell recognition domain is colored by lipophilic potential (LP). Water molecules within this interface in the 1BX2 crystal structure are shown as red spheres.

Within certain embodiments of the invention, substitution of one or more target hydrophobic residue(s) with one or more charged residue(s) (exemplified here by aspartate) provides the additional objective of constraining the modified RTL molecule to stay extended or "stretched" out along this interior β-strand by charge-charge repulsion, rather than allowing the structure to collapse onto itself in the absence of the Ig-fold domains that are present in the progenitor HLA-DR2 molecule. This conclusion is consistent with the data herein, and is additionally supported by reports that β-sheet propensity for an amino acid residue arises from local steric interactions of the amino acid side chain with its local backbone (Minor et al., *Nature* 367:660-63, 1994).

These instant results demonstrate that RTLs encoding the Ag-binding/TCR recognition domain of MHC class II molecules are innately very robust structures, capable of retaining activity separate from the Ig-fold domains of the progenitor class II structure, and even after fairly aggressive modification to make the molecules monomeric and monodisperse. Applying the methods and tools of the invention, increased solubility and prevention of aggregation of modified RTLs is readily accomplished by modification of a self-binding interface, motif, or residue(s), exemplified by an exposed surface of a native MHC class II structure that was originally buried in the progenitor protein structure. By staying within thermodynamic limitations that constrain the protein's final folded structure and by not interfering with the process by which the protein domain achieves this final fold, a key obstacle to recombinant design of monodisperse RTLs has been overcome—which is the requirement to leave intact within the primary sequence the "code" that drives folding toward a final unique structure that retains the ability to bind peptides and bind the TCR in an Ag-peptide-specific manner, retaining potent biological activity.

The following sections provide detailed guidance on the design, expression and uses of recombinant MHC molecules of the invention. Unless otherwise stated, standard molecular biology, biochemistry and immunology methods are used. Such standard methods are described in Sambrook et al. (1989), Ausubel et al (1987), Innis et al. (1990) and Harlow and Lane (1988). The following U.S. patents and additional patents and publications cited elsewhere herein relate to design, construction and formulation of MHC molecules and their uses, and are incorporated herein by reference to provide additional background and technical information relevant to the present invention: U.S. Pat. Nos. 5,130,297; 5,194,425; 5,260,422; 5,284,935; 5,468,481; 5,595,881; 5,635,363; 5,734,023.

Design of Recombinant MHC Class II β1α1 Molecules

The amino acid sequences of mammalian MHC class II α and β chain proteins, as well as nucleic acids encoding these proteins, are well known in the art and available from numerous sources, including references cited and incorporated herein, and GenBank. Within exemplary embodiments of the invention, modified RTLs may comprise a structurally-reduced or minimized MHC component that exclude all or part of a native MHC protein, for example all or part of an MHC class II β2 domain, or at least a CD4-binding portion of the β2 domain. Also typically excluded from the modified RTL is an α2 domain of the MHC class II protein. RTLs of this construction can be "empty" (i.e., free of peptide Ag), or non-covalently bound or covalently linked to peptide Ag. In more detailed aspects of the invention, the α1 and β1 MHC class II domains comprising the modified RTL may be linked together to foam a single chain (sc) polypeptide (Burrows et al., *Protein Engineering* 12:771-78; 1999; Chang et al., *J. Biol. Chem.* 276:24170-76, 2001).

Among the modified RTLs provided within the invention are exemplary constructs comprising recombinant MHC class II molecules, which in exemplary embodiments include the β1 domain of the MHC class II β chain covalently linked to the α1 domain of the MHC class II α chain. The β1 and α1 domains are well defined in mammalian MHC class II proteins. Typically, the α1 domain is regarded as comprising about residues 1-90 of the mature α chain. The native peptide linker region between the α1 and α2 domains of the MHC class II protein spans from about amino acid 76 to about amino acid 93 of the a chain, depending on the particular α chain under consideration. Thus, an α1 domain may include about amino acid residues 1-90 of the a chain, but one of skill in the art will recognize that the C-terminal cut-off of this domain is not necessarily precisely defined, and, for example, might occur at any point between amino acid residues 70-100 of the a chain. The composition of the α1 domain may also vary outside of these parameters depending on the mammalian species and the particular α chain in question. One of skill in the art will appreciate that the precise numerical parameters of the amino acid sequence are much less important than the maintenance of domain function.

Similarly, the β1 domain is typically regarded as comprising about residues 1-90 of the mature βb chain. The linker region between the β1 and β2 domains of the MHC class II protein spans from about amino acid 85 to about amino acid 100 of the β chain, depending on the particular chain under consideration. Thus, the β1 protein may include about amino acid residues 1-100, but one of skill in the art will again recognize that the C-terminal cut-off of this domain is not necessarily precisely defined, and, for example, might occur at any point between amino acid residues 75-105 of the β chain. The composition of the β1 domain may also vary outside of these parameters depending on the mammalian species and the particular β chain in question. Again, one of skill in the art will appreciate that the precise numerical parameters of the amino acid sequence are much less important than the maintenance of domain function.

Nucleic acid molecules encoding these domains may be produced by standard means, such as amplification by the polymerase chain reaction (PCR). Standard approaches for designing primers for amplifying open reading frames encoding these domain may be employed. Libraries suitable for the amplification of these domains include, for example, cDNA libraries prepared from the mammalian species in question; such libraries are available commercially, or may be prepared by standard methods. Thus, for example, constructs encoding the β1 and α1 polypeptides may be produced by PCR using four primers: primers β1 and β2 corresponding to the 5' and 3' ends of the β1 coding region, and primers A1 and A2 corresponding to the 5' and 3' ends of the α1 coding region. Following PCR amplification of the α1 and β1 domain coding regions, these amplified nucleic acid molecules may each be cloned into standard cloning vectors, or the molecules may be ligated together and then cloned into a suitable vector. To facilitate convenient cloning of the two coding regions, restriction endonuclease recognition sites may be designed into the PCR primers. For example, primers B2 and A1 may each include a suitable site such that the amplified fragments may be readily ligated together following amplification and digestion with the selected restriction enzyme. In addition, primers B1 and A2 may each include restriction sites to facilitate cloning into the polylinker site of the selected vector. Ligation of the two domain coding regions is performed such that the coding regions are operably linked, i.e., to maintain the open reading frame. Where the amplified coding regions are separately cloned, the fragments may be subsequently released from the cloning vector and gel purified" preparatory to ligation.

In particular embodiments, a peptide linker is provided between the β1 and α1 domains. Typically, this linker is between 2 and 25 amino acids in length, and serves to provide flexibility between the domains such that each domain is free to fold into its native conformation. The linker sequence may conveniently be provided by designing the PCR primers to encode the linker sequence. Thus, in the example described above, the linker sequence may be encoded by one of the B2 or A1 primers, or a combination of each of these primers.

Nucleic acid expression vectors including expression cassettes will be particularly useful for research purposes. Such vectors will typically include sequences encoding the dual domain MHC polypeptide (β1 α1) with a unique restriction site provided towards the 5' terminus of the MHC coding region, such that a sequence encoding an antigenic polypeptide may be conveniently attached. Such vectors will also typically include a promoter operably linked to the 5' terminus of the MHC coding region to provide for high level expression of the sequences.

In particular embodiments, β1 α1 molecules may also be expressed and purified without an attached peptide, in which case they may be referred to as "empty." The empty MHC molecules may then be loaded with the selected peptide as described below.

Sequence Variants.

One of skill in the art will appreciate that variants of the disclosed inventive molecules and domains may be made and utilized in the same manner as described. Thus, reference herein to a domain of an MHC polypeptide or molecule (e.g., an MHC class II β1 domain) includes both preferred forms of the referenced molecule, as well as molecules that are based on the amino acid sequence thereof, but which include one or more amino acid sequence variations. Such variant polypeptides may also be defined in the degree of amino acid sequence identity that they share with the disclosed preferred molecule. Typically, MHC domain variants will share at least 80% sequence identity with the sequence of the preferred MHC domains disclosed herein. More highly conserved variants will share at least 90% or at least 95% sequence identity with the preferred MHC domains disclosed herein. Variants of MHC domain polypeptides also retain the biological activity of the preferred MHC domains disclosed herein. For the purposes of this invention, that activity is conveniently assessed by incorporating the variant domain in the appropriate β1α1 polypeptide and determining the ability of the resulting polypeptide to inhibit antigen specific T-cell proliferation in vitro, as described in detail herein below.

Variant MHC domain polypeptides include proteins that differ in amino acid sequence from the preferred MHC domains disclosed herein, but which retain the specified biological and non-aggregating activity. Such proteins may be produced by manipulating the nucleotide sequence of the molecule encoding the domain, for example by site-directed mutagenesis or the polymerase chain reaction. The simplest modifications involve the substitution of one or more amino acids for amino acids having similar biochemical properties. These so-called conservative substitutions are likely to have minimal impact on the activity of the resultant protein. Table I shows amino acids which may be substituted for an original amino acid in a protein and which are regarded as conservative substitutions, which are well known in the art.

More substantial changes in biological function or other features may be obtained by selecting substitutions that are less conservative, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine. The effects of these amino acid substitutions or deletions or additions may be assessed through the use of the described T-cell proliferation assay.

At the nucleic acid level, one of skill in the art will appreciate that the naturally occurring nucleic acid sequences that encode class I and II MHC domains may be employed in the expression vectors, but that the invention is not limited to such sequences. Any sequence that encodes a functional MHC domain may be employed, and the nucleic acid sequence may be adapted to conform with the codon usage bias of the organism in which the sequence is to be expressed.

Modified RTLs of the invention exhibit a reduced capacity for self-aggregation compared to a corresponding, unmodified RTL (i.e., an RTL comprising only native MHC amino acid sequences). Therefore, the rational design of RTL surface modifications described herein yield an increased percentage of the RTL molecules present as monomers in solution compared to a monodisperse fraction of unmodified RTLs in solution.

Despite the surface structural changes introduced into the modified RTLs, these novel RTL constructs retain the ability to specifically bind Ag-peptides and to functionally interact with a TCR on a target T cell. Exemplary functions of the modified RTLs include an ability to modulate T cell activity in an Ag-specific manner to reduce a pathogenic potential or alter a pathogenic phenotype of the T cell (e.g., to inhibit T cell proliferation, reduce inflammatory cytokine production by the T cell, or increase anti-inflammatory cytokine production by the T cell). As such, the modified RTLs have utility to treat autoimmune diseases and other conditions mediated by antigen-specific T cells in vivo.

Within other aspects of the invention, modified RTLs are provided that lack trans-membrane Ig fold domains found in an intact MHC molecule, wherein the modified RTLs are non-aggregating or exhibit reduced aggregation compared to unmodified RTLs. The modified RTLs possess T cell regulatory activity as described herein, despite lacking certain structural features present in the corresponding, intact MHC molecule. MHC components of modified RTLs of the invention refold in a manner that is structurally analogous to native whole MHC molecules, and the bind peptide antigens to form stable MHC-antigen complexes.

Desired T cell responses that can be elicited, individually, in various combinations, or collectively, by the modified RTLs of the invention typically comprise one or more phenotypic change(s) that correlate(s) with an altered or "reprogrammed" state of a T cell associated with reduced pathogenic activity or potential (e.g., a reduced ability to mediate or potentiate autoimmune tissue destruction or other symptom(s) diagnostic of a selected autoimmune disease).

Modified RTL molecules of the invention are useful, for example, to detect, quantify and purify Ag-specific T-cells. In other embodiments, the modified RTLs are useful in compositions and methods to modulate T cell phenotype, activity, differentiation status, migration behavior, tissue localization, and/or cell fate. Within these aspects of the invention, compositions and methods are provided for modulating one or more T cell activities selected from T cell activation, proliferation, and/or expression of one or more cytokine(s), growth factor(s), chemokines, cell surface receptors (e.g., TCRs), and/or cellular adhesion molecules (CAMs). Properly designed, evaluated and administered, modified RTLs of the invention serve as potent T cell regulatory agents, in vitro or in vivo, to quantitatively modulate or qualitatively "switch" T cell phenotype-particularly with respect to pathogenic potential of the target T cell.

By contacting a target T cell with a modified RTL of the invention (bearing cognate antigen bound or linked to the TCR interface in the absence of costimulatory, factors (e.g., APCs and other regulatory signals as conferred by native, MHC II α2 and β2 regulatory sequences), the compositions and methods of the invention can function to "reprogram" a target T cell to alter the differentiation status or fate of the T cell, for example to an induced, nonpathogenic state or phenotype characterized by reduced pathogenic potential. For example, modified RTLs of the invention can be employed to reprogram a T cell from an original, pathogenic pathway of differentiation to one that yields a "T suppressor" phenotype. In additional embodiments RTLs of the invention can be employed to reprogram a T cell by eliciting a "switch" in one or more cytokines, or in a "cytokine expression profile", for example a switch from a Th1 to a Th2 cytokine expression profile, which in turn provides methods to reprogram T-cells to treat or manage autoimmune diseases and other disorders mediated by the T-cells. Additional description of these and related aspects of the invention is provided by Huan et al., $J.$ $Immunol.$ 172:4556-4566, 2004 (incorporated herein by reference).

Further uses for modified RTL constructs of the invention include, for example, evaluating T cell activity and function, or TCR function and binding specificity, in diagnostic and analytic contexts (see, e.g., Wang et al., $J.$ $Immunol.$) In more specific embodiments, RTLs of the invention can be used for detection, quantification and/or purification of T-cells that recognize particular antigens to yield important diagnostic and therapeutic information and materials. By way of example, early detection of T-cells specific for a particular autoantigen using, for example a labeled RTL, will facilitate early selection of appropriate treatment regimes. The ability to purify antigen-specific T-cells will also be of great value in adoptive immunotherapy. Adoptive immunotherapy involves the removal of T-cells, e.g., from a cancer patient, expansion of the T-cells in vitro and then reintroduction of the cells to the patient (see U.S. Pat. No. 4,690,915; Rosenberg et al. $New$ $Engl.$ $J.$ $Med.$ 319: 1676-1680 (1988)). Isolation and expansion of cancer specific T-cells with inflammatory properties will increase the specificity and effectiveness of immunological intervention.

In more detailed aspects of the invention, modified RTLs comprising a MHC class I or class II component is used in vivo to target and alter a pathogenic potential or activity of Ag-specific T cells. By way of example, a β1α1 molecule loaded with a T cell Ag (e.g., an antigenic epitope, domain, region, peptide, or other portion, derivative or conjugate of a T cell antigenic protein) and administered to patients suffering from multiple sclerosis or other autoimmune disease may be used to modulate T cell activity (e.g., modulate T cell proliferation, modulate T cell expression of one or more cytokine(s), chemokine(s), growth factor(s), and/or adhesion or other cell migratory factor(s), or induce anergy and/or phenotypic change(s) in T cell fate, differentiation status, location, bystander signaling or suppression activity, and/or pathogenic potential) in Ag-specific T cells—thereby alleviating or preventing associated disease symptoms. Alternatively, such molecules may be conjugated with a toxic moiety to directly kill disease-causing T cells.

The following examples set forth to provide those of ordinary skill in the art with a more detailed disclosure and description of the subject invention, and are not intended to limit the scope of what is regarded as the invention. Efforts have been made to ensure accuracy with respect to the numbers used (e.g., amounts, temperature, concentrations, etc.) but certain experimental errors and deviations should be allowed for.

Example 1

Methods

Homology Modeling.

Much of the logic for dissecting the molecules has been previously described (Burrows et al., $Protein$ $Engineering$ 12:771-78, 1999; Chang et al., $J.$ $Biol.$ $Chem.$ 276:24170-76, 2001). Sequence alignment of MHC class II molecules from human, rat and mouse species provided a starting point for our studies and graphic images were generated with the program Sybyl 6.9 (Tripos Associates, St. Louis, Mo.) on an O2 workstation (IRIX 6.5, Silicon Graphics, Mountain View, Calif.) using coordinates deposited in the Brookhaven Protein Data Bank (Brookhaven National Laboratories, Upton, N.Y.). Structure-based homology modeling was based on the refined crystallographic coordinates of human HLA-DR2 (Smith et al., $J.$ $Exp.$ $Med.$ 188:1511-20, 1998; Li et al., $J.$ $Mol.$ $Biol.$ 304:177-88, 2000), as well as DR1 (Brown et al., $Nature$ 364:33-39, 1993; Murthy et al., $Structure$ 5:1385-96, 1997), murine I-$E^k$ molecules (Fremont et al., $Science$ 272:1001-04, 1996), and scorpion toxins (Zhao et al., $J.$ $Mol.$ $Biol.$ 227:239-52, 1992; Housset et al., $J.$ $Mol.$ $Biol.$ 238:88-91, 1994; Zinn-Justin et al., $Biochemistry$ 35:8535-43, 1996). Amino acid residues in human HLA-DR2 (PDB accession code 1BX2) were used. This structure was determined by single wavelength diffraction and molecular replacement (AmoRe XRay/NMR structure refinement package, C.N.R.S., France) using HLA-DR1 as a starting structure (PDB accession code 1DLH) (Stern et al., $Nature$ 368:215, 1994). The following residues were either missing or had missing atoms in the final structure: chain A; K2, M36, K38, K39, E46, N78, R100, E101; chain B: E22, E35, E52, E59, K65, E69, P108, R189, (1BX2 numbering) (Smith et al., $J.$ $Exp.$ $Med.$ 188:1511-20, 1998). For these residues the correct side chains were inserted and the peptide backbone was modeled as a rigid body during structural refinement using local energy minimization.

RTL Structural Modification.

De novo synthesis of human HLA-DR2 derived RTLs has been previously described (Chang et al., J. Biol. Chem. 276:24170-76, 2001). Site-directed mutagenesis was used to replace hydrophobic residues on the solvent accessible surface of the β-sheet platform of the RTLs with polar (serine) or charged (aspartic acid) residues. The modification was performed by using the QuickChange™ site-directed mutagenesis method as described by Stratagene (La Jolla, Calif.). In brief, PCR reaction with Pfu DNA polymerase (Stratagene, La Jolla, Calif.) was performed by using RTL302 or RTL303 as template and two synthetic oligonucleotide primers containing the desired mutation(s). For example, a pair of mutation primers for RTL320 were 1) forward primer: 5'-GGC GAG TCA TCA AAG AAG AAC ATA GCA TCA GCC AGA GCG AGA GTT ATA GTA ATC CTG ACC AAT C-3' (SEQ ID NO: 1); 2) backward primer: 5'-GAT TGG TCA GGA TTA CTA TAA CTC TCG CTC TGG CTG ATG CTA TGT TCT TCT TTG ATG ACT C-3' (SEQ ID NO: 2); and a pair of mutation primers for RTL340 were 1) forward primer: 5'-GGC GAG TCA TCA AAG AAG AAC ATG ACA TCG ACC AGG ACG AGG ACT ATG ACA ATC CTG ACC AAT C-3' (SEQ ID NO: 3); 2) backward primer: 5'-GAT TGG TCA GGA TTG TCA TAG TCC TCG TCC TGG TCG ATG TCA TGT TCT TCT TTG ATG ACT C-3' (SEQ ID NO: 4). The oligonucleotide primers, each complementary to the opposite strand of template, were extended during 19 temperature cycles by means of Pfu DNA polymerase at an annealing temperature of 55° C. Upon incorporation of the oligonucleotide primers, a mutated plasmid containing staggered nicks is generated. Following temperature cycling, the PCR product was treated with DpnI endonuclease to digest the parental DNA template and to select for mutants containing the DNA sequence of interest. The nicked plasmid DNA incorporating the desired mutation(s) was then transformed into *E. Coli* BL21(DE3) as an expression host (Novagen, Madison, Wis.). Colonies were screened and cells containing plasmid with the desired mutation(s) were used for plasmid purification using QIAPREP® Spin Miniprep kit (QIAGEN, Valencia, Calif.). The purified plasmid DNA was then digested with NcoI and XhoI to confirm the efficiency of mutation. Finally, the desired plasmids were sequenced with the (T7) 5'-TAA TAC GAC TCA CTA TAG GG-3' (SEQ ID NO: 5) and (T7 terminal) 5'-GCT AGT TAT TGC TCA GCG G-3' (SEQ ID NO: 6) primers to confirm mutations of interest.

Expression and Refolding of Soluble RTL Molecules.

Expression, purification and refolding of human HLA-DR2 derived RTLs was previously described (Chang et al., J. Biol. Chem 276:24170-76, 2001). A number of modifications have been made in the protocol to streamline production while maintaining or slightly increasing the yield of protein. Bacteria were grown in one liter cultures to mid-logarithmic phase (OD600=0.6-0.7) in Luria-Bertani (LB) broth containing carbenicillin (50 µg/ml) at 37° C. Recombinant protein production was induced by addition of 0.5 mM isopropyl β-D-thiogalactoside (IPTG). After incubation for 4 hours, the cells were harvested by centrifugation and stored at 4° C. (short-term) or −80° C. (long-term) before processing. All subsequent manipulations of protein purification were at 4° C. The cell pellets were resuspended in lysis buffer (50 mM Tris-Cl, 0.1 M NaCl, 5 mM EDTA, pH 7.4). Lysozyme (10 mg/ml solution in lysis buffer; 1 mg per gram of cell pellet) was added, and the solution was incubated at room temperature for 30 minutes, swirling gently every 10 minutes. The cell suspension was then sonicated for 6×5 seconds with the cell suspension cooled in a salt ice water bath. The cell suspension was centrifuged (20,000 g for 10 minutes at 4° C., Beckman J2-21, JA-14 rotor), the supernatant fraction was poured off, the cell pellet resuspended and washed two times in 100 ml lysis buffer containing 1% TRITON® X-100 non-ionic surfactant and then one wash in lysis buffer without TRITON® X-100 non-ionic surfactant, and then resuspended in 100 ml Buffer A (20 mM ethanolamine, 6M urea, pH 10), and stirred gently at 4° C. overnight. After centrifugation (40,000 g for 45 minutes at 4° C., Beckman J2-21, JA-20 rotor), the supernatant containing the solubilized recombinant protein of interest was filtered (0.22µ STERICUP® filter unit, Millipore) and stored at 4° C. until purification. The recombinant proteins of interest were purified and concentrated by FPLC ion-exchange chromatography using Source 30Q anion-exchange media (Pharmacia Biotech, Piscataway, N.J.) in an XK26/20 column (Pharmacia Biotech), using a step gradient with buffer A and buffer B (20 mM ethanolamine/HCl, 6M urea, 2M NaCl, pH 10.0). Fractions containing the recombinant protein of interest were pooled and concentrated for size exclusion chromatography (SEC buffer, 20 mM ethanolamine, 6M urea, 0.2 M NaCl, pH 10.0; column, SUPERDEX® 75 matrix, HR16/60). Fractions containing protein of interest were pooled and diluted with SEC buffer to OD280 of 0.1. Proteins were dialyzed against 20 mM Tris-Cl at pH 8.5, which removed the urea and allowed refolding of the recombinant protein. Following dialysis, the proteins were concentrated by centrifugal ultrafiltration with CENTRICON® 10 membranes (Amicon, Beverly, Mass.). For purification to homogeneity, a finish step was included using size exclusion chromatography (SUPERDEX® 75 matrix, HR16/60). The final yield of purified protein varied between 15 to 30 mg/L of bacterial culture.

SDS-Gel Shift Assay.

Aliquots of purified protein sample were denatured by boiling for 5 min in Laemmli buffer with or without the reducing agent β-mercaptoethanol, and then analyzed by electrophoresis (12% SDS-PAGE). After electrophoresis, gels were stained with Coomassie brilliant blue (Sigma, St. Louis, Mo.) and destained for observation of molecular weight shifting.

Dynamic Light Scattering.

Dynamic light scattering (DLS) experiments were conducted with a DynaPro™ instrument (Protein Solutions, Inc., Charlottesville, Va.). The protein samples in 20 mM Tris-Cl buffer at pH 8.5 were filtered through 100 nm ANODISC™ membrane filter (Whatman, Clifton, N.J.) at a concentration of 1.0 mg/ml and 20 µl of filtered sample were loaded into a quartz cuvette and analyzed at 488 Dm. Fifty spectra were collected at 4° C. to get estimation of the diffusion coefficient and relative polydispersity of proteins in aqueous solution. Data were then analyzed by Dynamics software version 5.25.44 (Protein Solutions, Charlottesville, Va.) and buffer baselines were subtracted. Data were expressed as the mean of the calculated hydrodynamic radius. Molecular weights of RTLs were calculated assuming a globular hydrated shape for the molecules using Dynamics software version 5.25.44 (Protein Solutions, Charlottesville, Va.).

Circular Dichroism (CD) and Thermal Denaturation Analysis.

CD analysis and thermal denaturation studies were preformed as previously described (Chang et a., *J. Biol. Chem* 276:24170-76, 2001). In brief, recombinant proteins in 20 mM Tris-Cl buffer pH 8.5 were analyzed using an Aviv Model 215 CD spectrometer (Aviv Associates, Lakewood, N.J.). Spectra were the average of 4-5 scans from 260 to 180 nm, recorded at a scanning rate of 5 nm/min with 4-second time constant. Data were collected at 0.5 nm intervals. Spectra were averaged and smoothed using built-in algorithms and buffer baselines were subtracted. Secondary structure was estimated using a deconvolution software package (CDNN version 2.1, Aviv Associates, Lakewood, N.J.) based on the variable selection method (Compton et al., *Analytical Biochemistry* 155: 155-67, 1986). CD versus temperature (thermal denaturation curve) was recorded at a fixed wavelength of 208 nm. Temperature gradients from 60 to 95° C. were generated with a software controlled thermoelectric device to generate rising or falling temperature steps. Heating and cooling rates were between 10-12° C./h. The transition curves were normalized to 0 mdeg at 60° C. and are plotted as the change in absorbance (mdeg) as a function of temperature.

Enzyme Linked Immunosorbant Assay (ELISA).

Biotinylated MOG-35-55 peptide (Biot-MEVGWYR-SPFSRVVHLYRNGK-OH, SEQ ID NO: 7), non-biotinylated MOG-35-55 and MBP-85-99 peptide (ENPV-VHFFKNIVTPR-OH, SEQ ID NO: 8) were purchased from New England Peptide, Inc., (Fitchburg, Mass.). The purity of the peptides was verified by a reverse phase HPLC and mass identification was performed using MALDI-TOF to verify mass was within 0.1% of molecular weight expected. The peptides were lyophilized and stored at −80° C. until use. Direct binding assay experiments were carried out in order to determine the ability of the RTLs to bind peptide and to determine the concentration of the biotinylated peptide at which all specific binding sites were saturated under the conditions used in our studies. ELISA plates (Maxisorp, Nunc, Rochester, N.Y.) were coated with 50 µl of protein at a concentration of 1 µg/ml in 20 mM Tris, pH 8.5 (50 ng of protein; i.e., 40 nM) overnight at 4° C., washed 4 times with wash solution (0.05% Tween 20, PBS, pH 7.4), and blocked with a Casein solution (BioFX, Owing Mills, Md.) for 1.5 h at room temperature. Plates were then washed 4× and 50 µl of biotinylated peptide (serial dilutions) were added to the wells, RT, 1.5 h, and then washed 4×. 50 µl of a streptavidin-horseradish peroxidase conjugate (STR-HRP, 1:5000, DAKO, Glostrup, Denmark) in PBS was added to the wells and incubated at RT for 1.5 h then washed 4× to remove unbound conjugate. 50 µl of HRP substrate (BioFX) was added for 45 min, RT. Reactions were stopped with Stop Solution (BioFX) and bound peptide was determined indirectly by reading the absorbance at 405 nm in an ELISA plate reader (Applied Biosystems, Molecular Devices, Sunnyvale, Calif.). A standard curve of STR-HRP concentration vs $OD_{405}$ nm was used to determine the concentration of bound peptide. To control nonspecific binding, wells were coated with 3% non fat dry milk (NFDM) in PBS and treated in the same way as the RTL-coated wells. In order to determine the time required to reach steady-state binding of the peptides to the proteins, ELISA plates were coated, washed and blocked as above and then biotinylated peptide in PBS/1 mM EDTA at pH 7.4 at 0.15 µM was added at different times (0 to 36 h).

T Cell Clones and T Cell Proliferation Assay.

Antigen-specific T cell clones were selected from PBMC of an MS patient homozygous for HLA-DRB1*1501 as previously described (Burrows et al., *J. Immunol* 167:4386-95, 2001). Selected antigen-specific T cell clones were subcloned by limiting dilution method and subsequentially evaluated for antigen-specific proliferation (Burrows et al., *J. Immunol.* 167:4386-95, 2001) The clone with the highest stimulation index (SI) was selected and continuously cultured in RPMI medium supplemented with 1% human serum and 5 ng/ml IL-2. The clonality of cells was determined by RT-PCR with a clone defined as a T cell population utilizing a single TCR Vβ gene (Burrows et al., *J. Immunol* 167: 4386-95, 2001). T cell clones were expanded by stimulation with 1 µg/ml MOG-35-55 or MBP-85-99 peptide and $2 \times 10^5$ irradiated (2500 rad) autologous PBMCs per well in a 96-well plate. The expanded T cells were maintained in 1% human serum RPMI containing 5 ng/ml IL-2. Fresh IL-2 was added twice a week and T cell clones were restimulated with irradiated (2500 rad) autologous PBMCs every three weeks. Antigen-specific T cell proliferation were performed periodically to verify the quality of the cells. For these assays, antigen-specific T cell clones were washed twice with RPMI medium and $5 \times 10^4$ cells were re-seeded into each well in a 96-well plate and incubated in triplicate with $2 \times 10^5$ freshly isolated and irradiated (2500 rad) autologous PBMCs with 10 µg/ml of the desired peptide. Cells were incubated for 72 hours with [$^3$H]-thymidine added for the last 18 hours. Cells were harvested by a Harvester 96 (Tomtec, Hamden, Conn.) and radioactivity incorporated was measured on a 1205 BS liquid scintillation counter (Wallac, Turku, Finland), Stimulation index (SI) was calculated by dividing the mean cpm of peptide-added wells by the mean cpm of the medium alone control wells. In RTL treatment experiments, 8 µM of the desired RTL was pre-incubated with the T cell clones for 72 hours, following by two washes with RPMI media before the T cell proliferation assay was performed.

Mice.

HLA-DR2 Tg mice bearing chimeric MHC class II molecules were developed as previously described (Woods et al., *J. Exp. Med.* 180:173-81, 1994). The peptide-binding domain of MHC class II is encoded by human sequences while the membrane proximal portion including the CD4-binding domain is encoded by mouse sequences (DRα1*0101: I-Eα and DRβ1*1501: I-Eβ, previously described). The DRβ1*1501: I-Eβ construct was made essentially as described in Woods et al. (Woods et al., *J. Exp. Med.* 180:173-81, 1994), with the following changes: The pACYCI84 vector containing the DRB1*0401 exons 1 and 2, and the $Eβ^d$ exons 3-6 was partially digested with BamHI and treated with Klenow polymerase to remove a BamHI site in the vector. Subsequently, DRB1*1501 exon 2 was cloned into pACYC184 which had been predigested with BamHI and EcoRI to remove DRB1*0401 exon 2, Transgenic mice were generated by microinjecting the chimeric α- and β-chain constructs into fertilized eggs from (DBA/2×C57BL/6)F$_1$ matings. Viable embryos were transferred into pseudo pregnant females for development to term. Transgenic offspring were backcrossed twice to the MHC class II knock out mouse, MHCII$^{Δ/Δ}$ (Madsen et al., *Pro Natl Acad Sci USA* 96:10338-43, 1999).

Induction of Active EAE and Treatment with RTLs.

Tg HLA-DR2 male and female mice between 8 and 12 weeks of age were immunized subcutaneously as described (Ito et al., *J Immunol.* 167, 2001) at four sites on the flanks with 0.2 ml of an emulsion comprised of 200 µg mouse MOG-35-55 peptide in complete Freund's adjuvant (CFA) containing 400 µg *Mycobacterium tuberculosis* H37RA (Difco, Detroit, Mich.). In addition, mice were given pertussis toxin (Ptx, List Biological Laboratories, Campbell, Calif.) on Day 0 and Day 2 post-immunization (25 ng and 67 ng per mouse, respectively). Mice were treated i.v. daily for 8 days, beginning 2-4 days after onset of clinical signs, with 100 µl of RTL312, RTL342, or vehicle (20 mM Tris, pH 8.5) containing 33 µg of the RTL proteins. Actively immunized mice were assessed daily for clinical signs of EAE according to the following scale: 0=normal; 1=limp tailor mild hind limb weakness; 2=limp tail and moderate hind limb weakness or mild ataxia; 3=limp tail and moderately severe hind limb weakness; 4=limp tail and severe hind limb weakness or mild forelimb weakness or moderate ataxia; 5=limp tail and paraplegia with no more than moderate forelimb weakness; and 6=limp tail and paraplegia with severe forelimb weakness or severe ataxia or moribund condition. The average daily score was determined for each mouse by summing the daily clinical scores and dividing by the number of days the mouse exhibited clinical signs. The mean peak and average daily scores plus or minus SD were calculated for the control and experimental groups.

Example 2

Rationally Designed Mutations Converted Complexes of Human Recombinant T Cell Receptor Ligands into Monomers that Retained Biological Activity We have recently described protein engineering studies of recombinant TCR ligands (RTLs) derived from the alpha-1 and beta-1 domains of HLA-DR2 (DRB1*1501/DRA*0101) (Chang et al., *J. Biol. Chem.* 276:24170-76, 2001). These molecules formed well defined aggregates that were highly soluble in aqueous buffers, with retention of biological activity (Burrows et al., *J. Immunol.* 167:4386-95, 2001; Buenafe, *JBC*, 2003; Vandenbark et al., *Journal of Immunology*, 2003). We analyzed the membrane proximal surface of the β-sheet platform that packed on the membrane distal surfaces of the α2 and β2 Ig-fold domains, specifically looking for features that might contribute to higher-order structures or aggregation (FIG. 1).

FIG. 1 shows HLA-DR2, RTL302, and the solvent accessible surface of the RTL β-sheet platform. The left panel (A) shows a scale model of an MHC class II molecule on the surface of an APC. The right panel (B) shows RTL302, a soluble single-chain molecule derived from the antigen-binding if cell recognition domains. The structures are based on the crystallographic coordinates of HLA-DR2 (PDB accession code 1BX2), and the transmembrane domains are shown schematically as 0.5 nm cylinders. The amino and carboxyl termini of HLA-DR2 and RTL302 are labeled N, C, respectively. Disulfide bonds are displayed as ball and stick models. The lower right panel (C) shows the hydrophobic residues of the beta-sheet platform of RTL302. Beta-sheet strands are depicted in ribbon form and the hydrophobic residues are grouped based on their location within the beta-sheet platform and on their relative level of interaction with residues from the α2 and β2 Ig-fold domains. Group 1 residues VI02, I104, A106, F108, L110 comprised a central core along beta-strand 1 of the alpha-1 domain, and, peripheral to this core, L9 and M119. Group II residues F19, L28, F32, V45, and V51 were beta-1 domain residues and group III residues A133, V138 and L141 were from the alpha-1 domain.

We grouped these residues, based on their location within the beta-sheet platform and on their relative level of interaction with residues from the α2 and β2 Ig-fold domains, and constructed a series of site-directed mutants, replacing single and then multiple residues with either serine or aspartic acid residues. The study developed in two stages, with the first stage focused on obtaining soluble proteins that were monodisperse, and the second focused on biophysical and biochemical characterization of the modified molecules.

Reiterative site-directed mutagenesis allowed us to generate two modified RTLs that were suitable for further biological characterization (TABLE I).

TABLE I

Molecules used in this study

| Molecule | Description |
| --- | --- |
| RTL302 | Human HLA DR2 (DRB1*150101/DRA*0101) β1α1 domains |
| RTL302 (5S) | RTL302 (V102S, I104S, A106S, F108S, L110S)[a] |
| RTL302 (5D) | RTL302 (V102D, I104D, A106D, F108D, L110D) |
| RTL303 | RTL302/MBP-85-99[b] |
| RTL312 | RTL302/MOG-35-55[c] |
| RTL320 | RTL303 (5S) |
| RTL340 | RTL303 (5D) |
| RTL342 | RTL312 (5D) |

[a]RTL302 numbering. These residues correspond to HLA-DR2 alpha-chain residues V6, I8, A10, F12, and L14. Residue numbering is increased in the Ag-tethered molecules to account for the Ag-peptide (variable length) plus linker (15 residues).
[b]MBP-85-99, ENPVVHFFKNIVTPR (SEQ ID NO: 8)
[c]MOG-35-55, MEVGWYRSPFSRVVHLYRNGK (SEQ ID NO: 7)

RTL302 could be converted to a monomer with either five serine (5S) or five aspartate (5D) substitutions, RTL302(5S) and RTL302(5D), respectively, within a group of residues along the external face of the first strand of anti-parallel β-sheet derived from the alpha chain of the HLA-DR2 progenitor molecule. We have termed these the group I core residues (FIG. 1, left panel A). Comparison of the 5S or 5D modified molecules with RTL302 by size exclusion chromatography (SEC) (FIG. 2, upper panel A) demonstrated that both RTL302(5S) and RTL302(5D) behaved as approximately 25 kD monomers.

Figure 2:
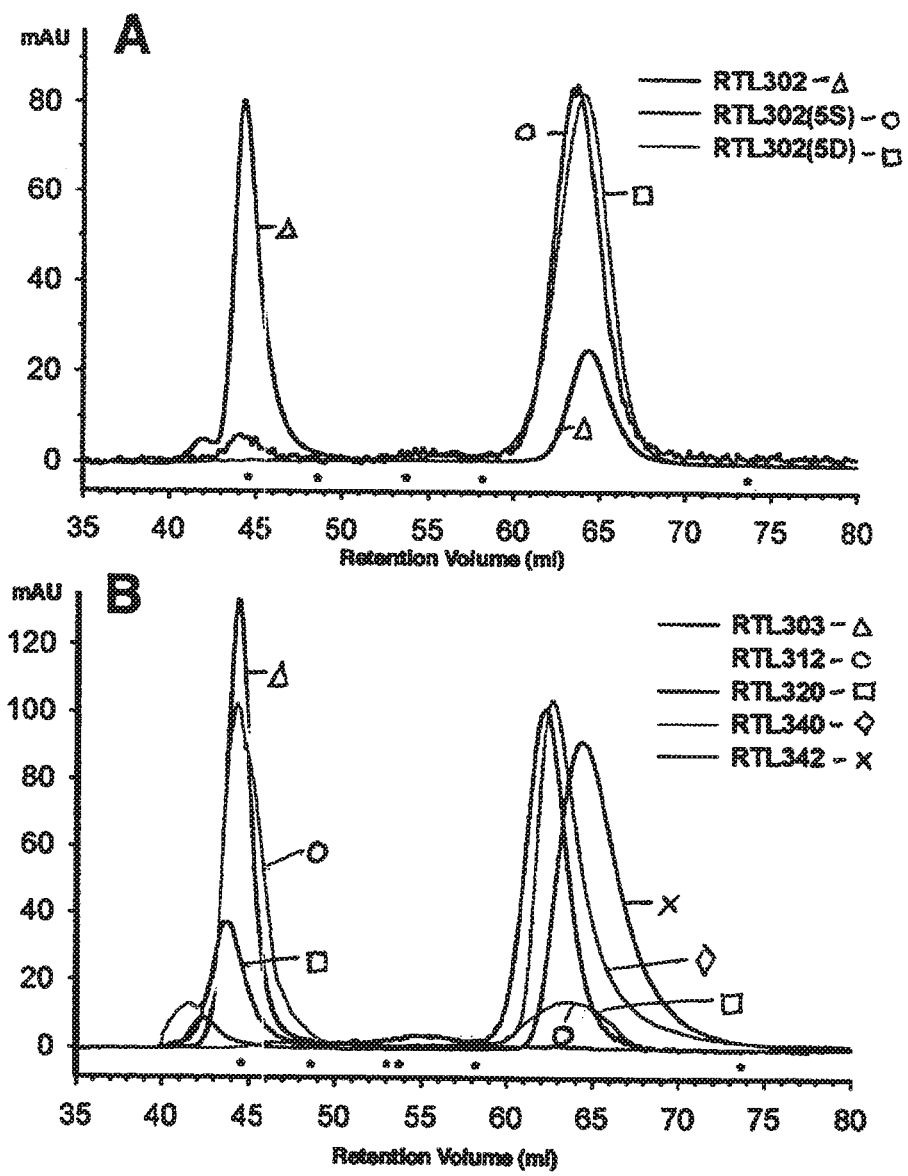
FIG. 2 shows size exclusion chromatography of modified RTLs. Purified and refolded RTLs were analyzed by size exclusion chromatography (SEC). The upper panel (A) shows SEC of RTL302 (triangle), RTL302(5S) (circle) and RTL302(5D) (square). These RTLs do not contain covalently tethered Ag-peptides. The lower panel (B) shows SEC of RTLs derived from the wild-type HLA-DR2 containing covalently tethered Ag-peptide MBP-85-99 (RTL303, triangle) or MOG-35-55 (RTL312, circle).

FIG. 2 shows size exclusion chromatography of modified RTLs. Purified and refolded RTLs were analyzed by size exclusion chromatography (SEC). The upper panel (A) shows SEC of RTL302, RTL302(5S) and RTL302(5D). These RTLs do not contain covalently tethered Ag-peptides. The lower panel (B) shows SEC of RTLs derived from the wild-type HLA-DR2 containing covalently tethered Ag-peptide MBP-85-99 (RTL303) or MOG-35-55 (RTL312). The 5S and 5D variants of RTL303 (RTL320, and RTL340, respectively) and the 5D variant of RTL312 (RTL342) are also displayed. The SUPERDEX® 75 matrix 16/60 size exclusion column was calibrated with a set of proteins of known molecular weight with exclusion volumes as indicated (*); Myoglobin, 17.3 kD; Ovalbumin, 43 kD; Bovine serum albumin 67 kD; Catalase 232 kD; thyroglobulin, 670 kD.

Dynamic light scattering (DLS), was used to measure the diffusion constants and calculate hydrodynamic radii for the molecules (Table II), and these studies demonstrated unequivocally that RTL302(5S) and RTL302(5D) were monomeric. When Ag-peptides were covalently tethered to the amino-terminus of the molecules, their properties varied slightly depending on the Ag-peptide used, and more importantly, differed depending on the presence of the polar 5S or charged 5D modifications. Comparing RTL320 (5S modification, covalently tethered MBP-85-99 peptide) with RTL340 (5D modification, covalently tethered MBP-85-99 peptide), RTL320 still tended to aggregate, with most of the molecules (85%) formed into multimers of approximately 5 molecules. RTL340 was completely monomeric, and was more robust in terms of being able to accommodate various covalently tethered Ag-peptides such as MBP-85-99 (RTL340) and MOG-35-55 (RTL342) without significant alteration in the solution properties of the RTLs (FIG. 2; Table II).

TABLE II

Hydrodynamic analysis of RTLs by Dynamic Light Scattering

| Molecule | Radius (nm) | Estimated MW(kD) | % of Mass in buffer |
|---|---|---|---|
| RTL302 (peak I)[a] | 17.6 | 2760 | 100 |
| RTL302 (peak II) | 2.5 | 27 | 100 |
| RTL302 (5S) | 2.5 | 27 | 98 |
| RTL302 (5D) | 2.3 | 25 | 100 |
| RTL303 | 15.4 | 2030 | 100 |
| RTL312 (peak I) | 15.2 | 1970 | 31 |
| RTL312 (peak II) | 4.3 | 102 | 69 |
| RTL320 (peak I) | 13.5 | 1490 | 100 |
| RTL320 (peak II) | 4.8 | 131 | 100 |
| RTL340 | 2.5 | 28 | 100 |
| RTL342 | 2.6 | 31 | 100 |

Hydrodynamic Status of modified RTLs were analyzed by light scattering analysis using a DynaPro ™ molecular sizing instrument (Protein Solutions, Inc.). [a]Some of the proteins showed two clearly defined peaks by SEC and these were characterized independently. Peak I refers to the aggregate (larger) peak, and peak II refers to the smaller size, in most cases monomeric fraction.

Further biochemical analysis demonstrated that the 5S- and 5D-modified molecules retained their native structure. RTLs contain a native conserved disulfide bond between cysteine 16 and 80 (RTL302 amino acid numbering, corresponding to HLA-DR2 beta-chain residues 15 and 79). Air oxidation of these residues to reconstitute the native disulfide bond was demonstrated by a gel shift assay in which identical samples with or without the reducing agent β-mercaptoethanol (β-ME) were boiled 5 minutes prior to SDS-PAGE. In the absence of β-ME disulfide bonds are retained and proteins typically demonstrate a higher mobility during electrophoresis through acrylamide gels due to their more compact structure. All of the RTL molecules produced showed this pattern, indicating the presence of the native conserved disulfide bond. These data represent a primary confirmation of the conformational integrity of the molecules.

Circular dichroism (CD) demonstrated the highly ordered secondary structures of the RTL constructs. The RTLs without covalently tethered Ag-peptide contained 20-25% alpha-helix, 21-27% anti-parallel beta-strand, and 20-22% beta-turn structures (FIG. 3A; Table III).

TABLE III

Secondary structure analysis of RTLs

| Molecule | α-Helix | α-Parellel β-Sheet | Parallel β-Sheet | B-turn | Random coil | Total |
|---|---|---|---|---|---|---|
| RTL302 (peak I) | 0.21 | 0.21 | 0.02 | 0.23 | 0.33 | 0.99 |
| RTL302 (peak II) | 0.20 | 0.27 | 0.00 | 0.20 | 0.32 | 0.99 |
| RTL302(5S) | 0.20 | 0.21 | 0.02 | 0.22 | 0.34 | 1.00 |
| RTL302(5D) | 0.20 | 0.27 | 0.00 | 0.20 | 0.20 | 1.00 |
| RTL303 | 0.26 | 0.20 | 0.04 | 0.19 | 0.32 | 1.00 |
| RTL312 | 0.18 | 0.24 | 0.07 | 0.17 | 0.31 | 0.96 |
| RTL320 (peak I) | 0.22 | 0.22 | 0.03 | 0.21 | 0.32 | 1.00 |
| RTL320 (peak II) | 0.19 | 0.19 | 0.03 | 0.23 | 0.35 | 1.00 |
| RTL340 | 0.15 | 0.20 | 0.03 | 0.27 | 0.35 | 1.00 |
| RTL342 | 0.19 | 0.22 | 0.05 | 0.18 | 0.30 | 0.93 |

Secondary structure content derived from the deconvoluted spectra of the RTLs presented in FIG. 3.

FIG. 3 shows circular dichroism (CD) spectra of modified DR2-derived RTLs. The upper panel (A) shows CD spectra of "empty" RTL302, RTL302(5S) and RTL302(5D). The middle panel (B) shows CD spectra of RTLs containing covalently tethered Ag MBP-85-99 peptide. RTL303, RTL320, and RTL340. The lower panel (C) shows thermal denaturation curves for RTL303, RTL320 and RTL340 show a high degree of cooperativity and stability. RTL340 was resistant to complete thermal denaturation and aggregation and is soluble even after boiling for 5 minutes. Unless otherwise indicated, CD measurements were pedal arced at 25° C. on an Aviv-215 instrument using 0.1 mm cell from 260 to 180 nM on protein samples in 20 mM Tris-Cl, pH 8.5. Concentration of each protein was determined by amino acid analysis. Data are expressed as Delta-epsilon per mole per cm. Analysis of the secondary structure was performed using the variable selection method (Compton et al., *Analytical Biochemistry* 155:155-67, 1986).

The RTLs with covalently tethered Ag-peptides contained 15-19% alpha-helix, 19-22% anti-parallel beta-strand, and 18-23% beta-turn structures (FIG. 3B; Table III). These three basic secondary structures of a polypeptide chain (helix, sheet, coil) each show a characteristic CD spectrum in the far UV, and a protein consisting of these elements displays a spectra that can be deconvoluted into each of the individual contributions. Although there are limitations inherent in the method (such as the lack of consideration of chromophore interaction(s) within different structural regions), the fit is quite acceptable for what would be expected for a qualitative assessment of the RTL protein fold and is consistent with our previous data collected for the multimeric versions of the RTLs (Chang et al., *J. Biol. Chem* 276:24170-76, 2001). The monodisperse monomeric RTLs retain the native structure of the progenitor Ag-binding/TCR recognition domain of HLA-DR2.

We also used CD to monitor structure loss upon thermal denaturation. The RTLs exhibited a high degree of thermal stability, and non-linear least-square analysis indicated that the RTLs described in this study are cooperatively folded (FIG. 3C). The temperature ($T_m$) at which half of the structure was lost in 20 mM Tris, pH 8.5, was difficult to determine because of the high melting temperatures observed. Extrapolation of the curves using non-linear analysis yields a $T_m$ of 92° C. for RTL303, 87° C. for RTL320 and 98° C. for RTL340. We had previously reported a $T_m$ for RTL303 of 78° C. when the molecule was solubilized in PBS (Chang et al., *J. Biol. Chem.* 276:24170-76, 2001) reflecting the effect solvent had on the overall stability of the molecules.

We used a "peptide capture" ELISA assay with biotinylated-MOG to compare Ag-peptide binding to RTL302, RTL302(5S), and RTL(5D). Non-linear regression analysis using a one-site (hyperbola) binding model was used to calculate a $B_{max}$ and $K_d$ for the molecules (FIG. 4A).

Figure 4:
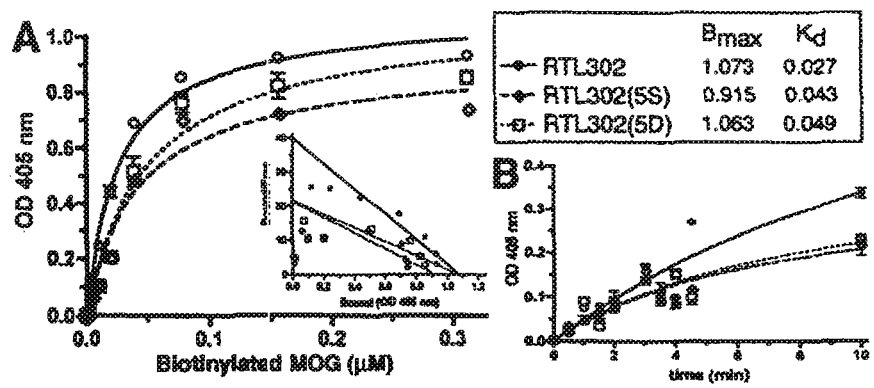
FIG. 4 shows direct measurement of peptide binding to HLA-DR2-derived RTLs. Binding of biotinylated-MOG to RTL302 (open circles), RTL302(5S) (open diamonds), and RTL302(5D) (open squares). The left panel (A) shows saturation as a function of biotinylated-MOG concentration (insert shows Scatchard analysis of peptide binding). The right panel (B) shows binding of biotinylated-MOG peptide (0.15 μM) to RTLs as a function of time to compare the initial rate of binding.

FIG. 4 shows direct measurement of peptide binding to HLA-DR2-derived RTLs. Binding of biotinylated-MOG to RTL302 (open circles), RTL302(5S) (open diamonds), and RTL302(5D) (open squares). The left panel (A) shows saturation as a function of biotinylated-MOG concentration (insert shows Scatchard analysis of peptide binding). The right panel (B) shows binding of biotinylated-MOG peptide (0.15 μM) to RTLs as a function of time to compare the initial rate of binding.

As shown in (FIG. 4B), binding of MOG peptide (0.15 μM) to RTLs as a function of time was extremely fast. Using linear regression analysis the initial rate of MOG binding was calculated to be 0.17±0.06 ΔOD/min for RTL302, 0.11±0.02 ΔOD/min for RTL302(5S), and 0.10±0.02 for RTL(5D).

We characterized the in vitro activity of the RTLs in an assay designed to quantify their ability to induce Ag-specific inhibition of T cell proliferation (Burrows et al., *J. Immunol.* 167:4386-95, 2001; Wang et al., *The Journal of Immunology*, 2003; Vandenbark et al., *Journal of Immunology*, 2003). The DR2-restricted T cell clone 4-G1 is specific for the MBP-85-99 peptide. Cells that were not pretreated with RTLs ("untreated" control) showed a 68× stimulation index and cells pretreated with "empty" RTL302 showed close to 90× stimulation index, a 31% increase above the "untreated" control. Pre-incubation with RTL303, RTL320 or RTL340 all showed greater than 90% inhibition of proliferation compared with the "untreated" control (TABLE IV).

TABLE IV

Antigen-specific inhibition of T cell proliferation by pre-incubating with RTLs

| Clone EN4-G1 | Pre-incubation | | | | |
|---|---|---|---|---|---|
| | Untreated | RTL302 | RTL303 | RTL320 | RTL340 |
| +APC alone | 588.97 | 569.1 | 578.7 | 592.0 | 641.9 |
| +APC/MBP85-99 (10 µg/ml) | 40144.67 | 50841.1 | 2560.4 | 1847.7 | 1515.8 |
| Stimulation Index | 68 | 89 | 4 | 3 | 2 |
| Inhibition (%) | — | +31.1 | −93.5 | −95.2 | −96.5 |

Each data point represents the average of triple wells from each treatment.

We have recently described MOG-35-55-induced experimental autoimmune encephalomyelitis (EAE) in DR2 (DRB1*1501) transgenic (Tg) mice (Vandenbark et al., *Journal of Immunology*, 2003). This animal model of multiple sclerosis (MS) was characterized as a moderately severe chronic disease with 100% penetrance. Characteristics of the disease include ascending paralysis marked by inflammatory, demyelinating CNS lesions. EAE was induced with MOG-35-55 peptide/CFA on day 0 plus Ptx on days 0 and 2, and the initial symptoms of disease could be observed beginning about 10 days after induction. To evaluate the clinical potential of the monomeric RTL342, we treated Tg-DR2 mice with MOG-induced EAE 2-4 days after onset of clinical signs with RTL312, RTL342, or vehicle alone (FIG. 5, and see also TABLE V).

Figure 5:
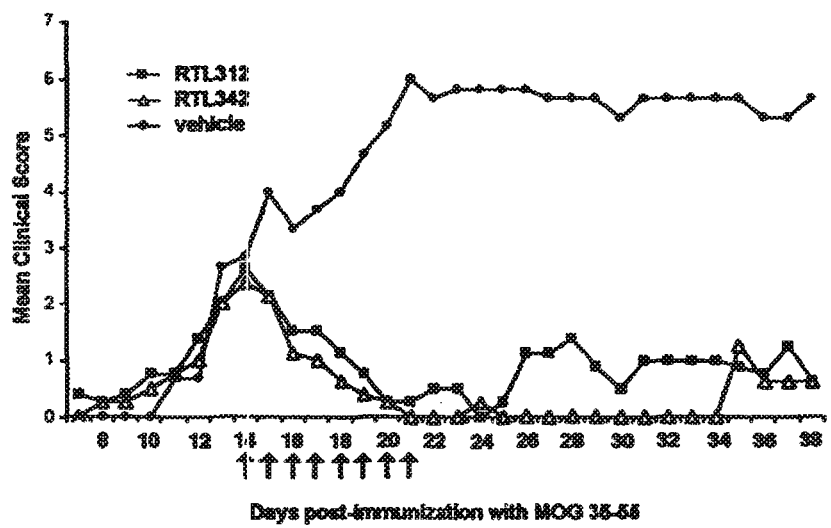
FIG. 5 shows that monomeric, monodisperse RTL342 was as effective as RTL312 at treating EAE in DR*1501 transgenic animals. Mean clinical scores of HLA-DR2 (DRB1*1501/DRA*0101) transgenic mice treated with 33 μg of RTL312 (v), RTL342 (Δ), or vehicle alone (Tris, pH 8.5) (●). All mice were immunized s.c. with 200 μg MOG-35-55 and 400 μg CFA in conjunction with 100 ng Ptx i.v. on Day 0 and 266 ng Ptx 2 days post-immunization. On Day 14 all mice were distributed into 6 groups according to similarity in disease and gender. Mice were i.v. injected daily with RTL312, RTL342, or vehicle. (n=4 per group, except for vehicle group where n=3; arrows indicate treatment).

FIG. 5 shows that monomeric, monodisperse RTL342 was as effective as RTL312 at treating EAE in DR*1501 transgenic animals. Mean clinical scores of HLA DR2 (DRB1*1501/DRA*0101) transgenic mice treated with 33 µg of RTL312 (▽), RTL342 (Δ), or vehicle alone (Tris, pH 8.5) (●). All mice were immunized s.c. with 200 µg MOG-35-55 and 400 µg CFA in conjunction with 100 ng Ptx i.v, on Day 0 and 266 ng Ptx 2 days post-immunization. On Day 14 all mice were distributed into 6 groups according to similarity in disease and gender. Mice were i.v. injected daily with RTL312, RTL342, or vehicle. (n=4 per group, except for vehicle group where n=3; arrows indicate treatment).

Treatment with RTL312 or RTL342 rapidly reversed established clinical signs of EAE (score about 2.5) to an average daily score of <0.5 units by the end of the eight-day treatment period. This low degree of disability was maintained without further RTL injections over the remainder of the observation period, which in one experiment lasted for 5 weeks after treatment was stopped. In contrast to the reversal of EAE mediated by RTL312 or RTL342, control groups receiving vehicle or 33 µg/injection of non-Ag-specified RTL303 (containing MBP-85-99 peptide) developed moderately severe chronic EAE (score of >4),

TABLE V

RTL treatment of DR2 Transgenic Mice

| Treatment | Incidence | Onset | Peak | Mortality | CDI |
|---|---|---|---|---|---|
| RTL312 | 4/4 | 9.5 ± 2.8 | 3 ± 1.8 | 0/4 | 29.8 ± 21.7* |
| RTL342 | 4/4 | 10.8 ± 2.2 | 2.6 ± 1.1 | 0/4 | 16 ± 10.9* |
| Vehicle | 3/3 | 12.3 ± 1.2 | 6 ± 0 | 0/4 | 133.7 ± 11.1 |

*= Significant difference between experimental group and vehicle group (p = 0.000)

Unless defined otherwise, all technical and scientific terms used herein have the same meaning as commonly understood by persons of ordinary skill in the art to which this invention pertains.

All publications mentioned herein are incorporated herein by reference for the purpose of describing and disclosing, for example, the methods and methodologies that are described in the publications which may be used in connection with the presently described invention. The publications discussed above and throughout the text are provided solely for their public disclosure prior to the filing date of the present application. Nothing herein is to be construed as an admission that the inventors are not entitled to antedate such disclosure by virtue of prior invention.

It will be understood by those skilled in the art that the foregoing description is intended to illustrate and not limit the scope of the invention defined in part by the appended claims and otherwise supported by the disclosure herein. Other aspects, advantages, and modifications of the current invention will be appreciated as embodied within the scope of the present disclosure, including but not limited to compositions, methods, devices and kits employing substantially similar or equivalent subject matter as described herein, which will be recognized as useful for practicing the invention and for implementing additional or alternative refinements, improvements, or related applications thereof.

What is claimed is:

1. A method of treating multiple sclerosis in a subject, comprising:
   administering to the subject a composition comprising a therapeutically effective amount of major histocompatibility complex-class II (MHC class II) component in the form of a single chain (sc) polypeptide comprising α1 and β1 domains of an HLA-DR protein, wherein the amino terminus of the α1 domain is covalently linked to the carboxy terminus of the β1 domain, wherein the MHC class II component does not include an α2 or β2 domain, and wherein the MHC class II component is modified by substitution of one or more hydrophobic residues with a polar or charged residue, wherein the one or more hydrophobic residues are selected from residues V6, I8, A10, F12, and L14 of the α1 domain; and
   an antigenic determinant, wherein the antigenic determinant is MOG 35-55.

2. The method of claim 1, wherein the α1 and β1 domains are coupled by a peptide linker.

3. The method of claim 1, wherein the antigenic determinant is covalently linked to the first domain of the MHC Class II component.

4. The method of claim 1, wherein the one or more hydrophobic residues are modified by substitution with a serine or aspartate residue.

5. The method of claim 1, wherein each of the residues V6, I8, A10, F12, and L14 of the α1 domain are modified by substitution with a serine or aspartate residue.

6. The method of claim 5, wherein each of the residues V6, I8, A10, F12, and L14 of the α1 domain are modified by substitution with a aspartate residue.

7. The method of claim 1, wherein the MHC Class II component further comprises substitution of one or more amino acids selected from the group consisting of L9, F19, L28, F32, V45, V51, A133, V138, and L141 with a polar or charged residue, wherein the amino acid position corresponds to positions in SEQ ID NO: 9.

8. The method of claim 1, wherein the β1 domain and the α1 domain are an HLA-DR2 β1 domain and an HLA-DR2 α1 domain.

9. A method of treating multiple sclerosis in a subject comprising administering to the subject a therapeutically effective amount of a polypeptide comprising SEQ ID NO: 9 in which one or more of amino acids V102, I104, A106, F108, and L110 are substituted with a polar or charged residue; and an antigenic determinant, wherein the antigenic determinant is MOG 35-55.

10. The method of claim 9, wherein the one or more hydrophobic residues are modified by substitution with a serine or aspartate residue.

11. The method of claim 9, wherein each of the residues V102, I104, A106, F108, and L110 of SEQ ID NO: 9 is modified by substitution with a serine or aspartate residue.

12. The method of claim 1, wherein the MHC class II polypeptide comprises SEQ ID NO: 9 and wherein the residues V6, I8, A10, F12, and L14 of the α1 domain corresponds to residues V102, I104, A106, F108, and L110 of SEQ ID NO: 9.

* * * * *

SEQUENCE LISTING

<160> NUMBER OF SEQ ID NOS: 11

<210> SEQ ID NO 1
<211> LENGTH: 64
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
ggcgagtcat caaagaagaa catagcatca gccagagcga gagttatagt aatcctgacc        60
aatc        64

<210> SEQ ID NO 2
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gattggtcag gattactata actctcgctc tggctgatgc tatgttcttc tttgatgact    60
c                                                                   61

<210> SEQ ID NO 3
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggcgagtcat caaagaagaa catgacatcg accaggacga ggactatgac aatcctgacc    60
aatc                                                                64

<210> SEQ ID NO 4
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gattggtcag gattgtcata gtcctcgtcc tggtcgatgt catgttcttc tttgatgact    60
c                                                                   61

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
taatacgact cactataggg                                                20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gctagttatt gctcagcgg                                                 19

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 7

Met Glu Val Gly Trp Tyr Arg Ser Pro Phe Ser Arg Val Val His Leu
1               5                   10                  15

Tyr Arg Asn Gly Lys
            20

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Asn Pro Val Val His Phe Phe Lys Asn Ile Val Thr Pro Arg
1               5                   10                  15

<210> SEQ ID NO 9
<211> LENGTH: 180
<212> TYPE: PRT
<213> ORGANISM: Homo sapiens

<400> SEQUENCE: 9

Met Gly Asp Thr Arg Pro Arg Phe Leu Trp Gln Pro Lys Arg Glu Cys
1               5                   10                  15

His Phe Phe Asn Gly Thr Glu Arg Val Arg Phe Leu Asp Arg Tyr Phe
                20                  25                  30

Tyr Asn Gln Glu Glu Ser Val Arg Phe Asp Ser Asp Val Gly Glu Phe
            35                  40                  45

Arg Ala Val Thr Glu Leu Gly Arg Pro Asp Ala Glu Tyr Trp Asn Ser
    50                  55                  60

Gln Lys Asp Ile Leu Glu Gln Ala Arg Ala Ala Val Asp Thr Tyr Cys
65                  70                  75                  80

Arg His Asn Tyr Gly Val Val Glu Ser Phe Thr Val Gln Arg Arg Val
                85                  90                  95

Ile Lys Glu Glu His Val Ile Ile Gln Ala Glu Phe Tyr Leu Asn Pro
            100                 105                 110

Asp Gln Ser Gly Glu Phe Met Phe Asp Phe Asp Gly Asp Glu Ile Phe
        115                 120                 125

His Val Asp Met Ala Lys Lys Glu Thr Val Trp Arg Leu Glu Glu Phe
    130                 135                 140

Gly Arg Phe Ala Ser Phe Glu Ala Gln Gly Ala Leu Ala Asn Ile Ala
145                 150                 155                 160

Val Asp Lys Ala Asn Leu Glu Ile Met Thr Lys Arg Ser Asn Tyr Thr
                165                 170                 175

Pro Ile Thr Asn
            180

<210> SEQ ID NO 10
<211> LENGTH: 178
<212> TYPE: PRT
<213> ORGANISM: Homo sapiens

<400> SEQUENCE: 10

Met Gly Asp Thr Pro Glu Asn Tyr Leu Phe Gln Gly Arg Gln Glu Cys
1               5                   10                  15

Tyr Ala Phe Asn Gly Thr Gln Arg Phe Leu Glu Arg Tyr Ile Tyr Asn

```
                20                  25                  30
Arg Glu Glu Phe Val Arg Phe Asp Ser Asp Val Gly Glu Phe Arg Ala
                35                  40                  45

Val Thr Glu Leu Gly Arg Pro Asp Glu Glu Tyr Trp Asn Ser Gln Lys
 50                  55                  60

Asp Ile Leu Glu Glu Glu Arg Ala Val Pro Asp Arg Met Cys Arg His
 65                  70                  75                  80

Asn Tyr Glu Leu Gly Gly Pro Met Thr Leu Gln Arg Arg Val Ile Lys
                 85                  90                  95

Ala Asp His Val Ser Thr Tyr Ala Ala Phe Val Gln Thr His Arg Pro
                100                 105                 110

Thr Gly Glu Phe Met Phe Glu Phe Asp Glu Asp Glu Met Phe Tyr Val
                115                 120                 125

Asp Leu Asp Lys Lys Glu Thr Val Trp His Leu Glu Glu Phe Gly Gln
130                 135                 140

Ala Phe Ser Phe Glu Ala Gln Gly Gly Leu Ala Asn Ile Ala Ile Leu
145                 150                 155                 160

Asn Asn Asn Leu Asn Thr Leu Ile Gln Arg Ser Asn His Thr Gln Ala
                165                 170                 175

Thr Asn

<210> SEQ ID NO 11
<211> LENGTH: 183
<212> TYPE: PRT
<213> ORGANISM: Homo sapiens

<400> SEQUENCE: 11

Met Arg Asp Ser Pro Glu Asp Phe Val Tyr Gln Phe Lys Gly Met Cys
 1               5                  10                  15

Tyr Phe Thr Asn Gly Thr Glu Arg Val Arg Leu Val Ser Arg Ser Ile
                20                  25                  30

Tyr Asn Arg Glu Glu Ile Val Arg Phe Asp Ser Asp Val Gly Glu Phe
                35                  40                  45

Arg Ala Val Thr Leu Leu Gly Leu Pro Ala Ala Glu Tyr Trp Asn Ser
 50                  55                  60

Gln Lys Asp Ile Leu Glu Arg Lys Arg Ala Ala Val Asp Arg Val Cys
 65                  70                  75                  80

Arg His Asn Tyr Gln Leu Glu Leu Arg Thr Thr Leu Gln Arg Arg Val
                 85                  90                  95

Glu Asp Ile Val Ala Asp His Val Ala Ser Tyr Gly Val Asn Leu Tyr
                100                 105                 110

Gln Ser Tyr Gly Pro Ser Gly Gln Tyr Thr His Glu Phe Asp Gly Asp
                115                 120                 125

Glu Gln Phe Tyr Val Asp Leu Gly Arg Lys Glu Thr Val Trp Cys Leu
                130                 135                 140

Pro Val Leu Arg Gln Phe Arg Gly Phe Asp Pro Gln Phe Ala Leu Thr
145                 150                 155                 160

Asn Ile Ala Val Leu Lys His Asn Leu Asn Ser Leu Ile Lys Arg Ser
                165                 170                 175

Asn Ser Thr Ala Ala Thr Asn
                180
```